US012765956B2

(12) United States Patent
Murray et al.

(10) Patent No.: US 12,765,956 B2
(45) Date of Patent: Oct. 20, 2026

(54) SMART SURGICAL INSTRUMENTS

(71) Applicant: GLOBUS MEDICAL, INC., Audubon, PA (US)

(72) Inventors: Patrick Murray, Collegeville, PA (US); Caelan Allen, North Wales, PA (US); Nicholas Meadows, Langhorne, PA (US); George Yacoub, Lansdale, PA (US)

(73) Assignee: Globus Medical, Inc., Audubon, PA (US)

(*) Notice: Subject to any disclaimer, the term of this patent is extended or adjusted under 35 U.S.C. 154(b) by 31 days.

(21) Appl. No.: 19/056,964

(22) Filed: Feb. 19, 2025

(65) Prior Publication Data

US 2026/0240618 A1 Aug. 20, 2026

(51) Int. Cl.

| | |
|---|---|
| ***A61B 34/35*** | (2016.01) |
| ***A61B 17/70*** | (2006.01) |
| *A61B 17/00* | (2006.01) |
| *A61B 90/00* | (2016.01) |

(52) U.S. Cl.

CPC .......... *A61B 34/35* (2016.02); *A61B 17/7074* (2013.01); *A61B 17/7082* (2013.01); *A61B 17/7086* (2013.01); *A61B 2017/00221* (2013.01); *A61B 2017/00725* (2013.01); *A61B 2017/00734* (2013.01); *A61B 2090/064* (2016.02); *A61B 2090/066* (2016.02); *A61B 2090/067* (2016.02)

(58) Field of Classification Search

CPC .. A61B 34/35; A61B 17/7074; A61B17/7082; A61B 17/7086; A61B 2090/064; A61B 2090/066; A61B 2090/067; A61B 2017/00221; A61B 2017/00725; A61B 2017/00734

USPC ......................................... 606/102, 104, 105

See application file for complete search history.

(56) References Cited

U.S. PATENT DOCUMENTS

| | | | |
|---|---|---|---|
| 5,586,907 A | 12/1996 | Frantz et al. | |
| 6,062,901 A | 5/2000 | Liu et al. | |
| 6,087,037 A | 7/2000 | Rieder | |
| RE37,226 E | 6/2001 | Wheeler et al. | |
| 6,739,068 B1 * | 5/2004 | Rinner ................. | A61B 17/025 33/783 |
| 7,550,213 B2 | 6/2009 | Wheeler et al. | |
| 7,591,672 B2 | 9/2009 | Wu | |
| 8,252,001 B2 | 8/2012 | Quirno et al. | |
| 8,414,593 B2 | 4/2013 | Quirno | |
| 9,364,249 B2 | 6/2016 | Kimball et al. | |

(Continued)

FOREIGN PATENT DOCUMENTS

| | | |
|---|---|---|
| CN | 2596560 Y | 12/2003 |
| CN | 202027587 U | 11/2011 |

(Continued)

*Primary Examiner* — Jessica Weiss

(57) ABSTRACT

Smart surgical instruments, systems, and methods for correcting a spinal deformity. The smart instruments are configured to sense and measure data, for example, related to screw insertion torque, segmental and global spine stiffness, correction force, rod reduction force, spinal alignment, or other metrics, which provide objective intraoperative data to the surgeon in real time. This data helps ensure that each action taken during the surgery is as precise as possible, minimizing risks and improving the effectiveness of the intervention.

12 Claims, 42 Drawing Sheets

(56) References Cited

U.S. PATENT DOCUMENTS

| | | | | |
|---|---|---|---|---|
| 9,585,700 | B2 * | 3/2017 | Wehrle | A61B 17/7083 |
| 9,743,971 | B2 * | 8/2017 | Belkoff | B25B 23/1405 |
| 10,065,315 | B2 | 9/2018 | Gulhar et al. | |
| 10,172,662 | B2 | 1/2019 | Gustafson et al. | |
| 10,405,935 | B2 | 9/2019 | McGahan et al. | |
| 10,456,211 | B2 | 10/2019 | McAfee | |
| 10,575,140 | B2 | 2/2020 | DiSilvestro et al. | |
| 10,675,094 | B2 * | 6/2020 | Crawford | A61B 34/10 |
| 10,828,079 | B2 | 11/2020 | Vikinsky et al. | |
| 10,925,619 | B2 | 2/2021 | Anderson | |
| 11,071,599 | B2 | 7/2021 | Brierton et al. | |
| 11,432,885 | B2 | 9/2022 | Shelton, IV et al. | |
| 11,612,420 | B2 * | 3/2023 | Nelsen | A61B 17/7086 606/264 |
| 11,653,990 | B2 | 5/2023 | Hares | |
| 11,701,196 | B2 | 7/2023 | Scheib et al. | |
| 11,877,721 | B2 | 1/2024 | Sholev et al. | |
| 12,029,516 | B2 * | 7/2024 | Soto | A61B 34/76 |
| 12,089,857 | B2 | 9/2024 | Buttin et al. | |
| 12,121,230 | B2 * | 10/2024 | Bechtold | A61B 17/1675 |
| 12,178,663 | B2 | 12/2024 | Zucker et al. | |
| 2013/0072982 | A1 * | 3/2013 | Simonson | A61B 17/7083 606/267 |
| 2016/0235494 | A1 | 8/2016 | Shelton, IV et al. | |
| 2017/0056075 | A1 | 3/2017 | Annadanam et al. | |
| 2017/0312039 | A1 * | 11/2017 | Crawford | A61B 90/98 |
| 2018/0279993 | A1 * | 10/2018 | Crawford | A61B 8/4218 |
| 2020/0405421 | A1 | 12/2020 | Luck | |
| 2024/0341855 | A1 * | 10/2024 | Murray | A61B 34/20 |

FOREIGN PATENT DOCUMENTS

| | | | |
|---|---|---|---|
| CN | 102648870 | A | 8/2012 |
| CN | 106361404 | A | 2/2017 |
| CN | 114642503 | A | 6/2022 |
| CN | 117041900 | A | 11/2023 |
| DE | 202010000341 | U1 | 6/2010 |
| DE | 102010015890 | A1 | 9/2011 |
| EP | 2011442 | A1 | 1/2009 |
| KR | 101886933 | B1 | 8/2018 |
| WO | 2012061718 | A1 | 5/2012 |

* cited by examiner

SMART SURGICAL INSTRUMENTS

FIELD OF THE INVENTION

The present disclosure generally relates to surgical instruments for a medical procedure, such as a spinal correction, and in particular smart surgical instruments that measure torque, spine stiffness, compression, or other metrics during a spinal procedure.

BACKGROUND OF THE INVENTION

Bone quality is an important parameter that surgeons consider when making a surgical plan to correct spinal deformities. The quality of a patient's bone can dictate which correction maneuvers can be performed and what amount of correction can be expected. Bone density influences implant purchase and therefore how hard the surgeon is able to push or pull on the bone during correction. Implants, such as pedicle screws, have a better and more stable connection when inserted into healthy dense bone, whereas implants have a weaker and less stable connection when inserted into osteoporotic or weak bone. Surgeons need to push or pull on the bones to achieve correction, so they must know the bone quality of the patient in order to perform safe correction. Most surgeons currently assess patient bone quality intraoperatively by feeling tactile feedback during screw insertion and/or by tugging on the screws after insertion. However, this method is subjective and relies on surgeon experience. They must then use this feeling to make a judgement about how much force they can safely place on that patient during correction.

It would be beneficial for the surgeon to have an instrument that can assess the quality of the bone screw interface. Studies have shown that screw insertion torque is related to screw pullout force. Therefore, an instrument that measures screw insertion torque and compression would provide valuable information to the surgeon by giving them an objective measurement of the quality of the bone screw interface. The surgeon would then be able to make more informed decisions regarding correction strategies without relying solely on feel. Thus, there exists a need for instruments providing surgical instrumentation metrics or other relevant data to the surgeons during the surgical procedure.

SUMMARY OF THE INVENTION

To meet this and other needs, smart surgical instruments, systems, and methods are provided. In particular, the smart surgical instruments are configured to measure intraoperative real-time data related to bone-screw interface strength, correction force, spine stiffness and/or other quantitative data in order to aid the surgeon throughout the surgical procedure. The smart surgical instruments give surgeons accurate assessments of screw insertion torque, segmental and global spine stiffness, correction force, rod reduction force, or other metrics, and provide the surgeon with useful means of analyzing the data in order to make safe and effective decisions during surgery.

According to one embodiment, a smart surgical system for correcting a spinal deformity includes a smart instrument including a force-sensing assembly configured to sense and measure intraoperative real-time data while the instrument is in use during a surgical procedure. The force-sensing assembly includes an enclosure housing a load cell with one or more sensors to accurately measure force electronically connected to a printed circuit board assembly configured to wirelessly transmit signals. The smart instrument includes a battery cartridge receivable in the enclosure of the force-sensing assembly configured to power the printed circuit board assembly. The system includes a robot system configured to receive the signals transmitted from the printed circuit board assembly. The real-time data is communicated to the user to provide guidance during the surgical procedure.

The smart surgical system may include one or more of the following features. The real-time data may include screw insertion torque, segmental and/or global spine stiffness, correction force, and/or rod reduction force. The battery cartridge may include a battery enclosure with a pair of metal blades protruding outward, a contact pad coupled to each respective metal blade with a screw, and a battery positioned between the contact pads. The battery cartridge may include a protruding arm with a hook configured to mate with a corresponding notch in the force-sensing assembly to securely couple the battery cartridge to the force-sensing assembly. The smart instrument may include battery lead components for electrically connecting the battery cartridge to the printed circuit board assembly. The battery lead components may include metal contacts each having a U-shaped body which form a receptacle to accept the respective metal blades of the battery cartridge, and metal pass throughs that connect the metal contacts to the printed circuit board assembly. The system may further include a communication dongle configured to receive signals transmitted by the force-sensing assembly. The communication dongle may include an enclosure, a printed circuit board assembly, and a battery. The system may utilize a first communication dongle connected directly to the robot system and a second communication dongle used simultaneously for redundant transfer of data.

According to one embodiment, a smart screw driver instrument for correcting a spinal deformity includes a driver shaft with a distal tip configured to engage with an implant, a force-sensing adapter assembly configured to sense and measure torque and compression loads in real-time, and a battery cartridge receivable in the enclosure of the force-sensing adapter to power the force-sensing adapter. The force-sensing adapter assembly includes an enclosure, a male connection end for connecting a handle, a female connection end for connecting the driver shaft, a load cell to accurately measure force without permanent deformation, and a printed circuit board assembly electronically connected to the load cell. The load cell includes a torque sensing portion and a compression sensing portion.

The smart screw driver instrument may include one or more of the following features. The torque sensing portion may have an area of decreased diameter with strain gages mounted to an outer surface of the load cell. The compression sensing portion may have a through hole cut transversely to a long axis of the load cell and relief cuts positioned symmetrically around the through hole with strain gages mounted on the outer surface of the load cell between and within the relief cuts. The load cell may include a thin walled tube positioned within an inner cannulation of the load cell. The female connection end may include a collar defining a central bore dimensioned to fit a sleeve and a collet therein. The sleeve may include a cylindrical hollow tube which receives a portion of the collet. The collet may include exterior threads, which thread into corresponding threads within the bore of the collar. The collet may be configured to translate axially relative to the sleeve. The collet may include ball bearings, and when in a locked position, the sleeve is translated proximally such that the ball bearings partially protrude into an inner diameter of the collet, and when in an unlocked position, the sleeve is translated distally such that the ball bearings retract into the collet. The male connection end may include a shaft attached to the load cell via a threaded connection at one end and a free end at the other with an attachment interface for securing the handle. The driver shaft, the load cell, and the handle may be aligned along a common tool axis.

According to one embodiment, a smart rod reduction instrument for correcting a spinal deformity includes a rod pusher, a force-sensing adapter assembly, a battery cartridge, an access tower, and a locking cap driver. The rod pusher is configured to push a spinal rod into an implant. The force-sensing adapter assembly is configured to sense and measure mechanical loads in real-time. The force-sensing adapter assembly includes a mechanical housing including a pair of half nuts configured to engage or disengage from the rod pusher and a load cell configured to accurately measure force without permanent deformation, and an electronic housing including a printed circuit board assembly electronically connected to the load cell. The battery cartridge is receivable in the electronic housing to power the force-sensing adapter. The access tower is configured for coupling the force-sensing adapter to the implant. The locking cap driver is positionable through the rod pusher.

The smart reducer instrument may include one or more of the following features. When an axial force is applied in a distal direction, the half nuts may be forced into an open state disengaged from the rod pusher, and when an axial force is applied in a proximal direction, the half nuts may be forced into a locked state engaged with the rod pusher. The half nuts may each have a semi-cylindrical body defining interior threads configured to engage corresponding threads on the rod pusher. The half nuts may include pins along an outer surface, which fit into corresponding slots through a wall of the mechanical housing. The slots may have a V-shape configured to translate the respective half nuts toward or away from a centerline of the instrument. The half nuts may be spring-loaded axially toward the load cell via a spring. The rod pusher may be supported within the electronic housing by a central shaft that couples to the load cell at one end and a tightening nut at an opposite end. The rod pusher may include a longitudinal rod pusher shaft with an externally threaded section configured to interface with the half nuts and a rod advancer with a distal rod-contacting end sized and dimensioned to contact the spinal rod. The mechanical housing may include a pair of keying prongs configured to fit into the access tower and a pair of release clips that secure the housing to the access tower. The electrical housing may be contained within an offset handle, which is laterally offset from a remainder of the instrument.

According to another embodiment, a smart rod reducer instrument system for correcting a spinal deformity includes a surgical robotic and navigation system having an on-board computer with software executed by one or more processing units, a force-sensing instrument, and a battery cartridge. The force-sensing instrument is configured to sense and measure mechanical loads in real-time while the instrument is in use. The force-sensing instrument includes a rod pusher configured to push a spinal rod into an implant, a mechanical housing including a pair of half nuts configured to engage or disengage from the rod pusher and a compression load cell with one or more strain gages configured to accurately measure strain on the load cell, and an electronic housing including a battery recess having metal contacts coupled to a printed circuit board assembly that wirelessly communicates with the surgical robotic and navigation system. The battery cartridge is receivable in the battery recess to power the force-sensing instrument.

The smart rod reducer instrument system may include one or more of the following features. When a force is exerted on the rod pusher during reduction of the spinal rod, a rod reduction force may be determined from the one or more strain gages, which is wirelessly communicated to the surgical robotic and navigation system. The half nuts may be configured to interact with the load cell such that force is transmitted from the half nuts to the load cell. The electronic housing may include an upper enclosure half containing the metal contacts and pass through and a lower enclosure half containing the printed circuit board assembly, and the rod pusher may pass through the lower enclosure half. The printed circuit board assembly may be connected to light-emitting diode lights configured to communicate information to a user.

According to another embodiment, a smart spreader instrument system for correcting a spinal deformity may include a surgical robotic and navigation system having an on-board computer with software executed by one or more processing units, a force-sensing instrument, and a battery cartridge. The force-sensing instrument includes two pivotable arms connected by a hinge with distal tips configured to engage the spine, a navigation array with reflective markers for instrument tracking by the surgical robotic and navigation system, an electronic housing containing a printed circuit board assembly configured to wirelessly transmit signals, and a stop mechanism with a reflective marker. The force-sensing instrument is configured to measure strain data in real-time to measure spine stiffness between different levels of the spine and track the positions of the stop mechanism and the instrument during use. The battery cartridge is receivable in the electronic housing of the force-sensing instrument to power the force-sensing instrument. The robotic and navigation system may receive the strain data from the force-sensing instrument to calculate the applied force and position data from the markers to calculate the deflection, and stiffness may be calculated as the applied force divided by the deflection. The reflective marker may be on the stop mechanism to allow the system to track the distance the distal tips are open. The stop mechanism may include a threaded shaft between the pivotable arm with a nut threaded onto the threaded shaft on an outside of one arm and configured to hold a force at the distal tips. The battery cartridge may include a pair of metal blades, a contact pad coupled to each respective metal blade with a screw, and a battery positioned between the contact pads. The electronic housing may include metal contacts configured to accept the metal blades of the battery cartridge, and metal pass throughs that connect the metal contacts to the printed circuit board assembly.

According to another embodiment, a smart orientation sensing instrument system for correcting a spinal deformity includes a smart instrument configured to sense and measure intraoperative real-time data during a surgical procedure. The smart instrument contains an inertial measurement unit, a microcontroller, a wireless communication module, and a battery. The inertial measurement unit includes an accelerometer, a gyroscope, and a magnetometer that captures data related to movement, rotation, and orientation. The system includes a patient fixation device for rigidly securing the smart instrument to a spine of a patient. The system includes a robot system configured to receive data transmitted from the smart instrument. The real-time data is communicated to the user to provide guidance during the surgical procedure.

The smart orientation sensing system may include one or more of the following features. The inertial measurement unit may provide nine degrees of freedom by measuring acceleration, angular velocity, and magnetic field data in three-dimensional space. During the surgical procedure, any change in position and/or orientation of the smart instrument may be measured and communicated to the surgeon by the robot system, thereby providing alignment of the spine intraoperatively. The patient fixation device may be a bone clamp or a lamina plate with screws. The system may further include a calibration jig attachable to a robot arm of the robot system, and the smart instrument is attachable to the calibration jig to calibrate the accelerometer, gyroscope, and magnetometer based on movements by the robot arm.

According to yet another embodiment, a kit may include a plurality of instruments or components thereof of different types and configurations. The kit may further include one or more implants, such as bone screws including screw extenders, spinal rods, or other devices suitable for correcting a spinal deformity.

BRIEF DESCRIPTION OF THE DRAWINGS

The present embodiments will become more fully understood from the detailed description and the accompanying drawings, wherein.

DETAILED DESCRIPTION

Embodiments of the disclosure are generally directed to smart instruments, systems, and methods for spine deformity correction. In particular, smart surgical instruments may be equipped with data-measurement capabilities, which allow the surgeon to obtain real-time data during surgery. The smart surgical instruments may measure a variety of parameters, such as torque applied during screw insertion, the pressure exerted on tissues, the angles of implant placement, and the forces applied during corrective procedures. For example, the smart surgical instruments may measure screw insertion torque, segmental and global spine stiffness, correction force, rod reduction force, or other quantitative data. This data helps ensure that each action taken during the surgery is as precise as possible, minimizing risks and improving the effectiveness of the intervention.

The smart surgical instruments may be part of larger surgical systems, for example, that include imaging, robotic and/or navigation technologies. The integration of data across these systems provides a comprehensive view of the surgical field, enhancing the surgeon's ability to plan, execute, and adjust the procedure dynamically. By leveraging precise measurements, surgeons can reduce the likelihood of complications, shorten surgery times, and enhance recovery rates by ensuring that each surgical action is optimized for the best possible outcome for the patient. Although generally described for use with spinal procedures and correcting a spinal deformity, it will be readily appreciated by those skilled in the art that the instruments may be employed in any number of suitable orthopedic approaches or other surgical procedures.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments or modifications thereof are contemplated as falling within the scope of this disclosure and equivalents thereto.

Figure 1:
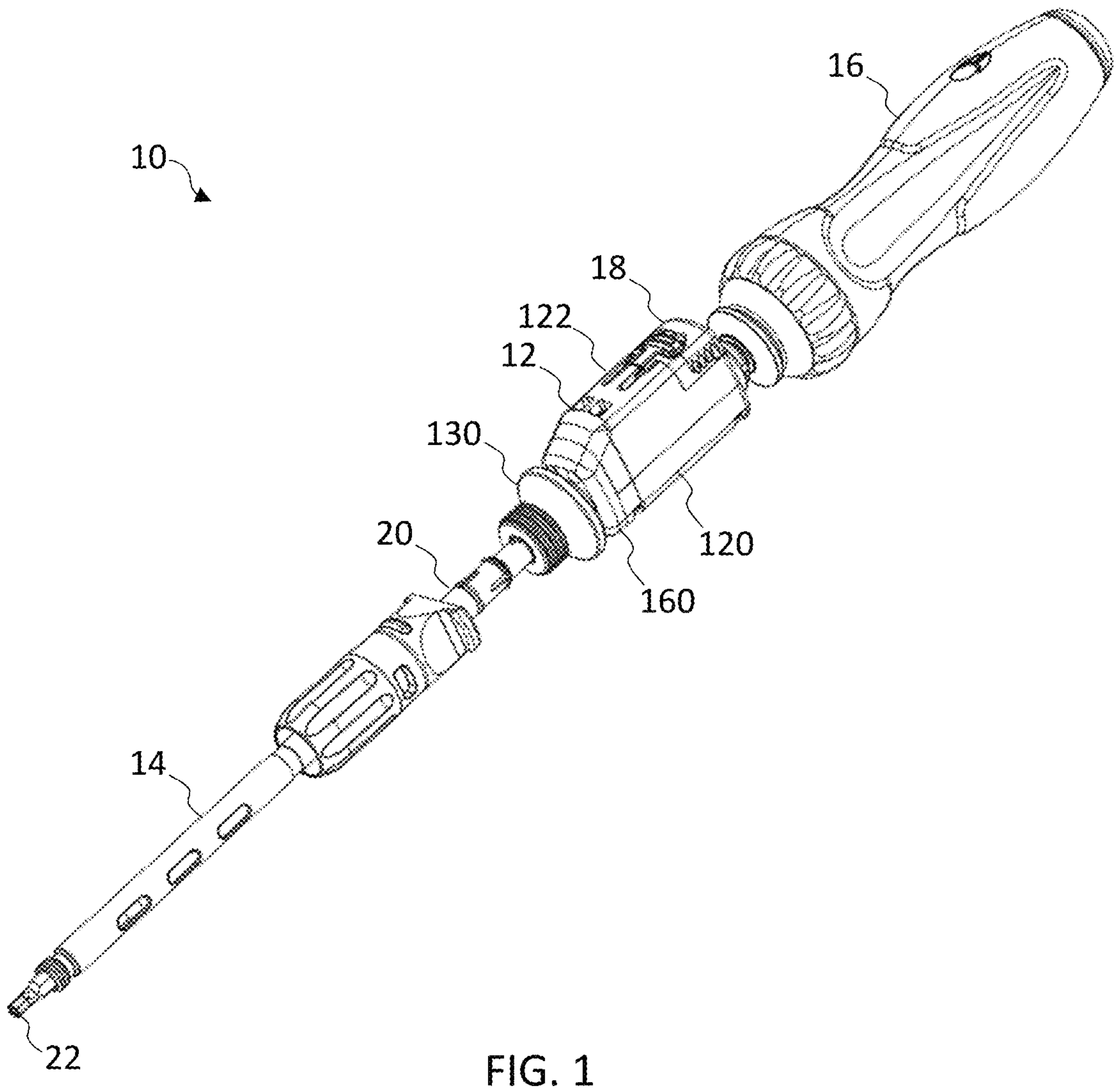
FIG. 1 illustrates a smart screwdriver assembly instrument with an adapter for measuring axial torque and axial compression loads according to one embodiment.

Turning now to the drawing, where like numerals can indicate like elements throughout, FIG. 1 illustrates a smart screwdriver instrument 10 according to one embodiment. The smart instrument 10 may be equipped with a torque/compression sensing adapter 12, which measures axial torque and axial compression loads while in use. Screw insertion torque reflects the amount of rotational force required to insert a screw into the vertebral bone, and may be directly related to screw pullout force. This measurement may help with assessing the appropriateness of screw size, the density of the bone, and the risk of screw loosening or over-tightening. To ensure that screws are securely and properly placed without causing damage to the bone, the smart instrument 10 measures screw insertion torque and compression to provide valuable information to the surgeon by giving them an objective measurement of the quality of the bone screw interface. The surgeon may then make informed decisions regarding correction strategies based on this objective data.

The smart screwdriver instrument 10 includes adapter assembly 12 coupled at one end to the driver assembly 14 and at the opposite end to the handle 16. The adapter assembly 12 is configured to receive a battery cartridge 18, which powers the smart screwdriver 10 and other smart surgical instruments. The adapter 12 is configured to sense and measure torque and compression loads exerted by the user through the instrument 10. The driver assembly 14 may include a screw driver shaft 20 with a distal drive tip 22 configure to mate with a driver engagement recess in the implant (e.g., a screw) to apply torque to the implant. The screw driver shaft 20 engages with the adapter assembly 12 such that the adapter assembly 12 exerts torque and/or compression on the screw driver shaft 20 when force or torque is applied to the handle 16 by the user. The adapter assembly 12 measures the force and/or torque exerted on the screw during insertion or other parts of the procedure and communicates the data to the user.

Battery Cartridge

Figure 2A:
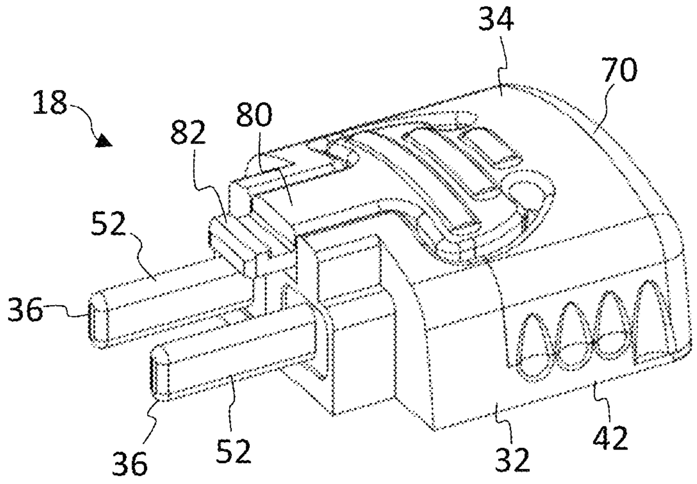
FIGS. 2A-2B show assembled and exploded views, respectively, of a battery cartridge for powering smart surgical instruments according to one embodiment.
Figure 2B:
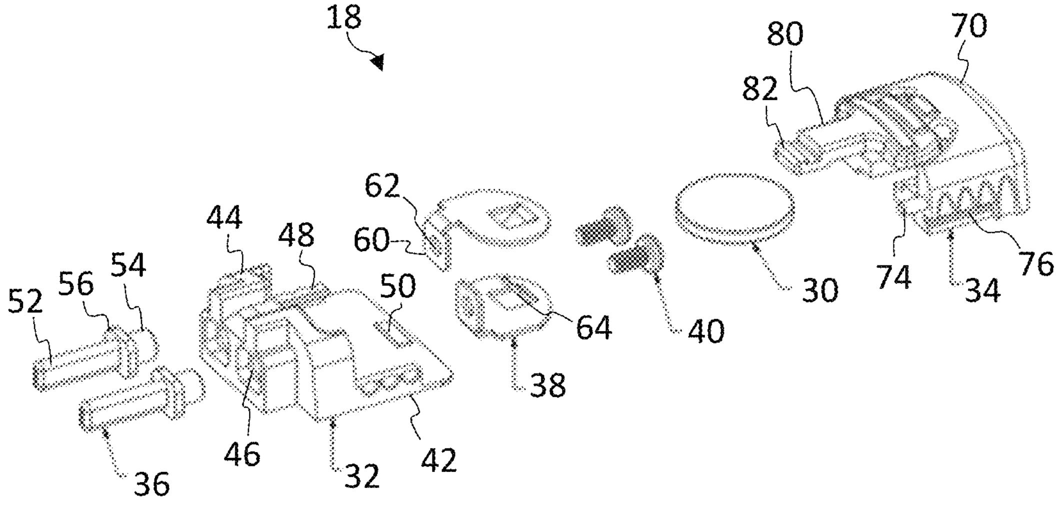

Turning now to FIGS. 2A-2B, the battery cartridge 18 is shown in more detail. The battery cartridge 18 includes a battery 30, two enclosure halves 32, 34, two metal blades 36, two contact pads 38, and two assembly screws 40. The battery enclosure 32, 34 holds and supports the components of the battery cartridge 18. The lower enclosure half 32 includes a flat base 42 with a wall 44 defining openings or through holes 46 for receiving the respective blades 36. For example, the lower enclosure half 32 may include two pockets with through holes 46 to accept the metal blades 36. The opposite side of the lower enclosure half 32 may include additional pockets to accept the two contact pads 38. The wall 44 may define pin holes or blind holes 47 configured to align the upper enclosure half 34 to the lower enclosure half 32. Each lateral side of the lower enclosure half 32 may define a rail 48 protruding from the base 42. The rails 48 are configured to couple the upper enclosure 34 to the lower enclosure 32. For example, the rails 48 may include an L-shaped protrusion for mating with T-slot geometry on the upper enclosure 34. A boss 50 may also protrude from the base 42 to further secure the enclosure parts together.

Figure 3:
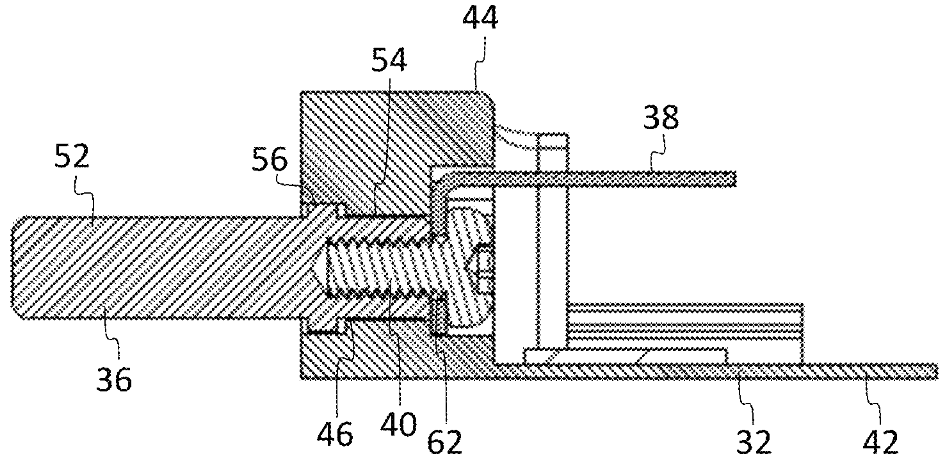
FIG. 3 shows a cross-section of the battery cartridge with the contact pad secured to the metal blade.
Figure 4:
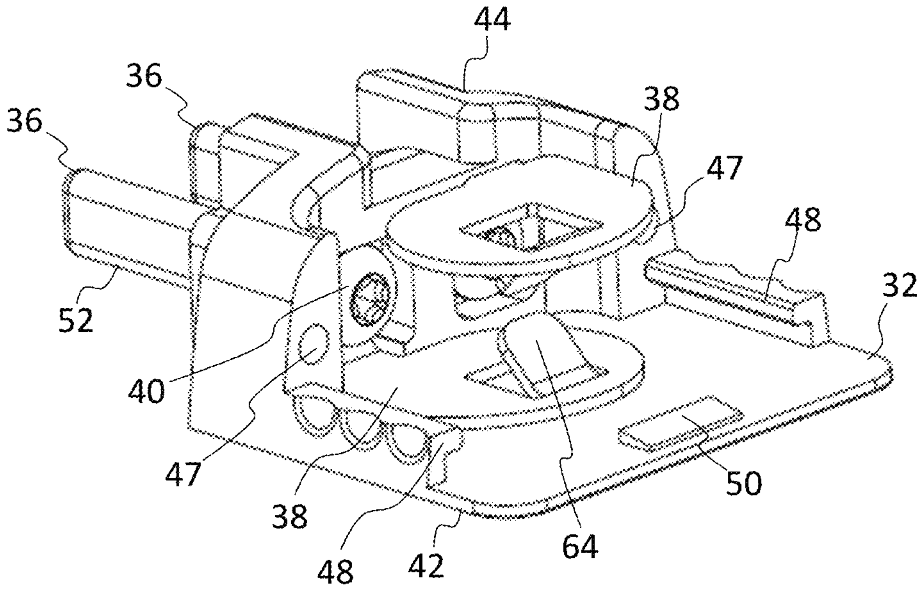
FIG. 4 shows the battery cartridge with the upper enclosure half and battery hidden to show the contact pads coupled to the metal blades and positioned within the lower enclosure half.

The metal blade 36 may include a flattened or elongated contact end 52 configured to protrude outward from the enclosure 32 and an opposite connecting end 54, which fits in the through hole 46 in wall 44 of the enclosure 32. A shoulder 56 may separate the contact end 52 from the connecting end 54. The connecting end 54 of the blade 36 defines a threaded recess 58 for receiving tip of screw 40 therein. As best seen in FIG. 3, one contact pad 38 is secured to each metal blade 36 with threaded screw 40. The contact pad 38 may have a thin L-shaped body with a mounting tab 60 defining an opening 62 for receiving the screw 40 therethrough. The contact pads 38 are positioned such that one is positioned vertically offset from the other. As best seen in FIG. 4, the two contact pads 38 do not touch each other. Each contact pad 38 has a portion 64 which is bent toward the middle plane of the lower enclosure half 32. The contacting tab 64 is configured to contact the battery 30. The metal blades 32 and contacting pads 38 may be made from a conductive metal, such as copper, brass, or stainless steel, for electrical conductivity and resistance to corrosion.

Figure 5A:
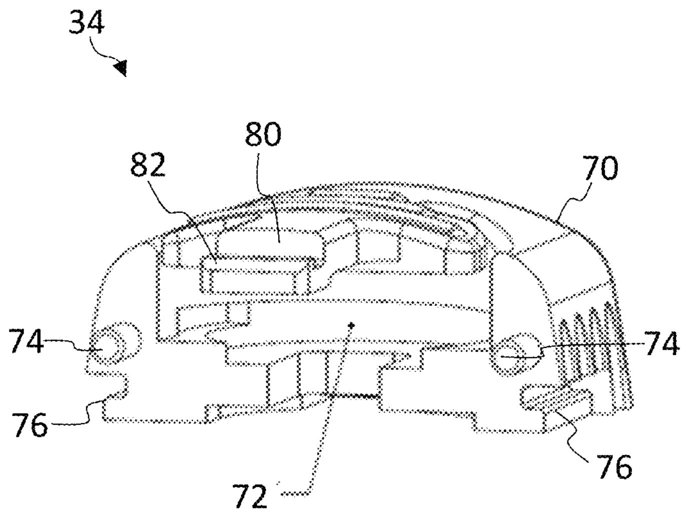
FIGS. 5A-5B illustrate a pocket within the upper enclosure half and a battery positioned within the pocket, respectively.
Figure 5B:
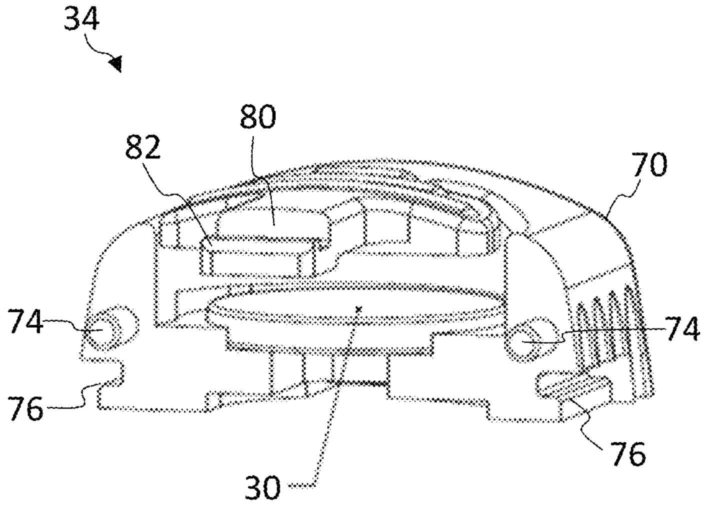
Figure 6A:
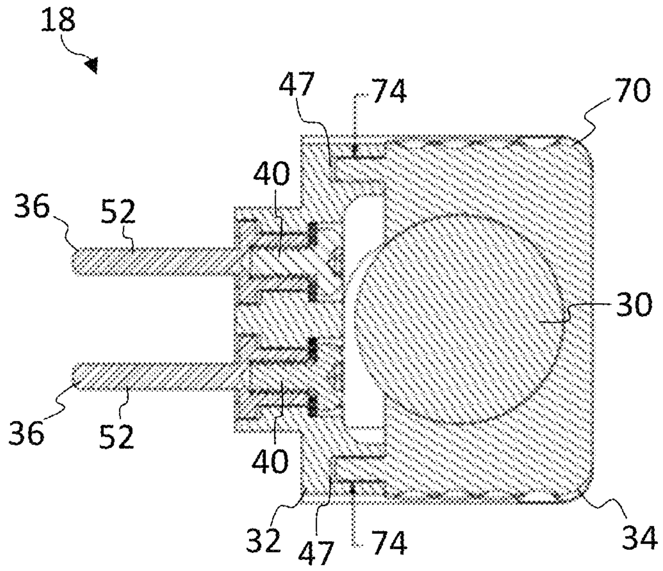
FIGS. 6A-6B show a cross-sectional views, respectively, showing the posts on the upper enclosure half positioned within the blind holes in the lower enclosure half, and showing the mating T-slot geometry between the upper and lower enclosure halves.
Figure 6B:
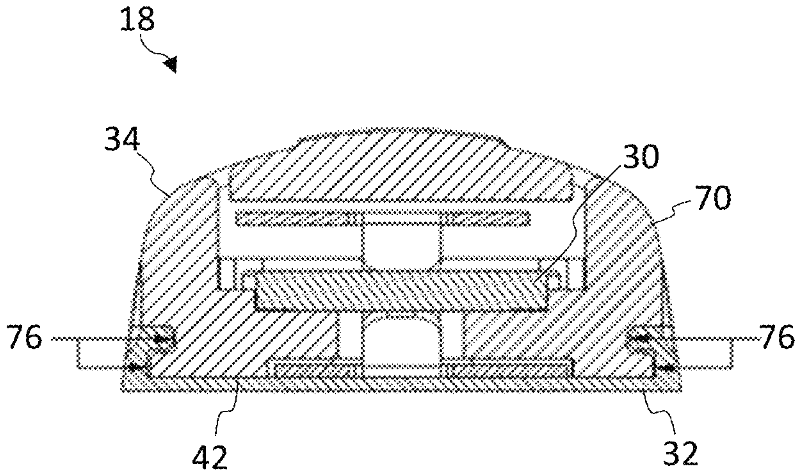
Figure 7A:
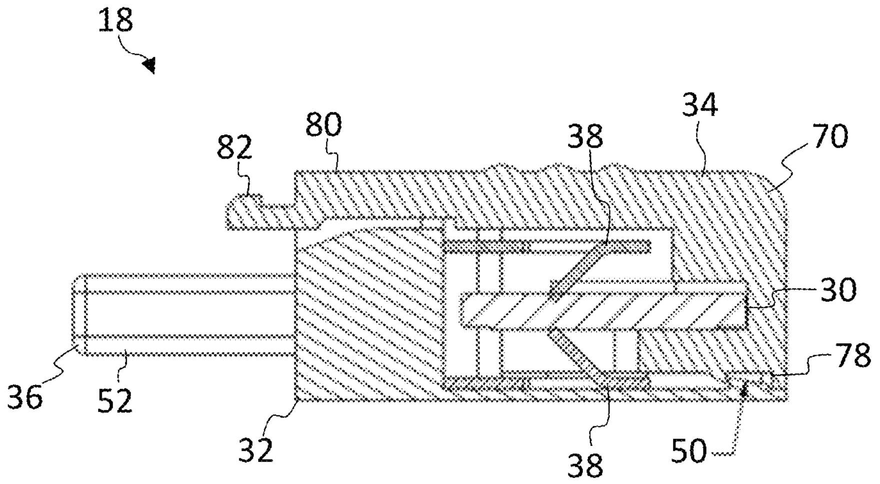
FIGS. 7A-7B show cross-sectional views including a close-up view of the boss on the lower enclosure half positioned within the pocket on the upper enclosure half.
Figure 7B:
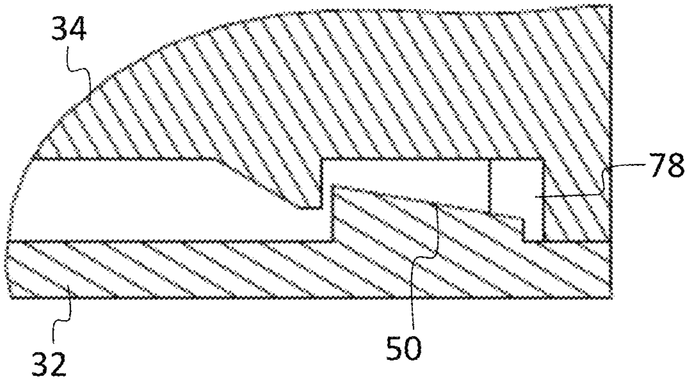

With further emphasis on FIGS. 5A-5B, the upper enclosure half 34 serves as the top cover 70 to enclose the components within the fully assembled enclosure 32, 34 of the battery cartridge 18. The upper enclosure half 34 has a pocket 72 sized and dimensioned to receive the battery 30. The battery 30 may be a coin cell battery, for example, with lithium chemistry or other suitable chemistry. The upper enclosure half 34 is configured to mate with the lower enclosure half 32 when assembled together. As best seen in FIG. 6A, the upper enclosure half 34 has forward protruding pins 74 (e.g., cylindrical pins) configured to be received within blind holes 47 in the lower enclosure half 32 to ensure proper alignment between the two components 32, 34. As best seen in FIG. 6B, the upper enclosure half 34 may also include T-slot geometry 76 on the lower surface to engage with mating T-slot geometry (e.g., rails 48) on the lower enclosure half 32 during assembly. The T-slot geometry 76 ensures a rigid connection between the two enclosure halves 32, 34 after assembly. In addition, the upper enclosure half 34 may have a pocket 78 configured to receive the boss 50 on the lower enclosure half 32 during assembly (see e.g., FIGS. 7A-7B). The boss 50 may be sized to have an interference fit with the upper enclosure half 34 such that the two enclosure halves 32, 34 must be pressed together to overcome the interference. After the two enclosure halves 32, 34 are fully engaged, the boss 50 on the lower enclosure half 32 falls into the pocket 78 on the upper enclosure half 34, securing the two halves 32, 34 together and preventing disassembly.

Figure 8A:
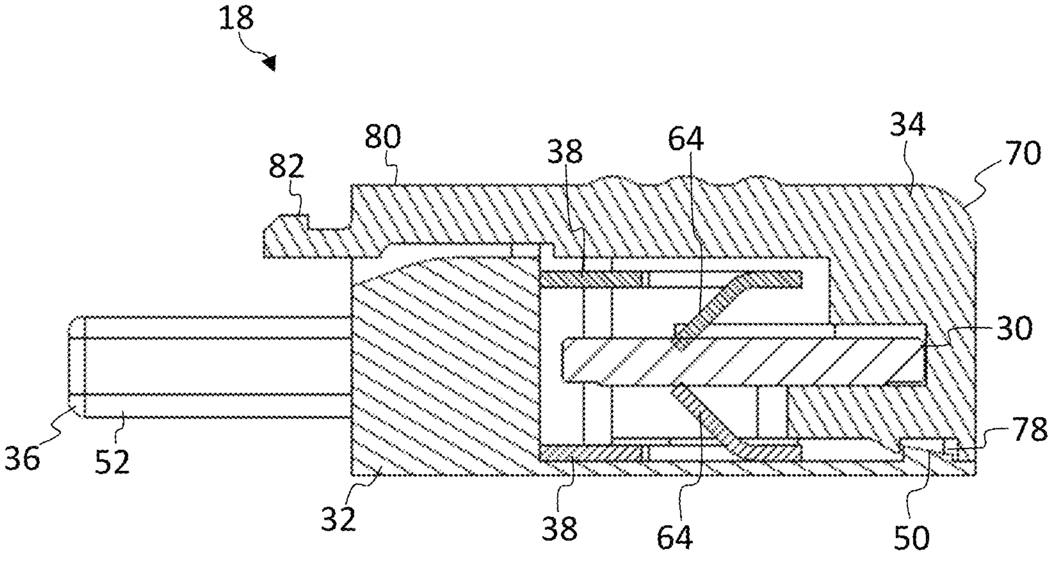
FIGS. 8A-8B show cross-sectional views of the bent portions of each contact pad touching opposite sides of the battery, and an arm protruding from the upper enclosure half to secure the battery cartridge in the smart instrument.
Figure 8B:
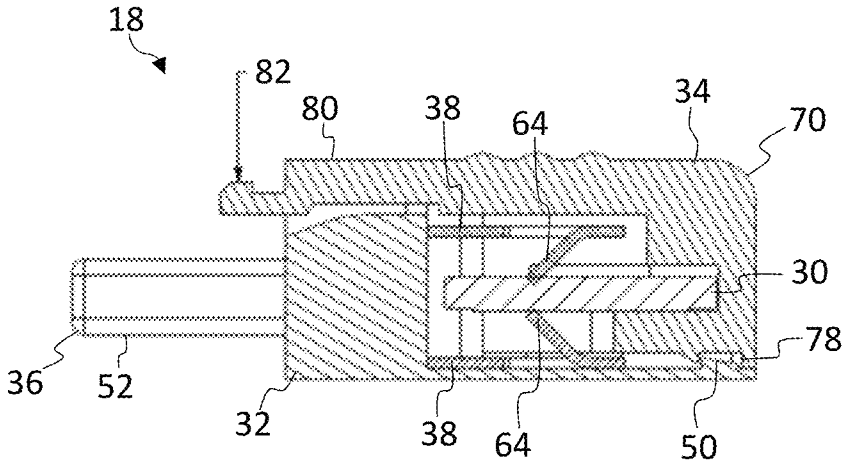
Figure 9:
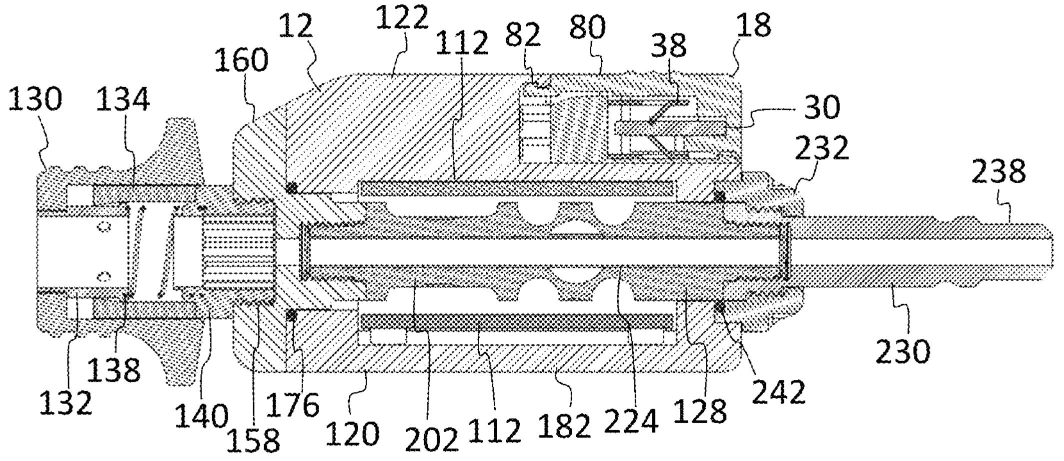
FIG. 9 shows a cross-sectional view of the battery cartridge assembled to the smart screwdriver instrument.
Figure 10:
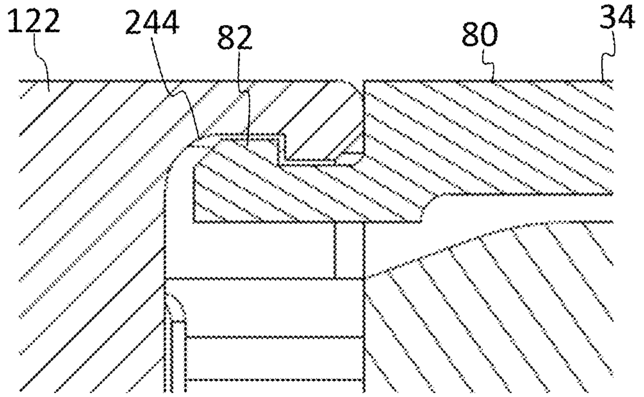
FIG. 10 is a close-up view of the arm of the battery cartridge engaging the smart instrument assembly.

After assembly, the battery 30 is positioned between the two contact pads 38. As shown in FIG. 8A, the bent portion 64 of each contact pad 38 is contacting opposite sides of the battery 30. Since the contact pads 38 are independently coupled to the metal blades 36, each metal blade 36 is linked to one side of the battery 30. As best seen in FIG. 8B, the upper enclosure half 34 has a forward protruding arm 80 with a hook 82 to mate with a notch 244 on the adapter assembly 12 in order to securely couple the battery cartridge 18 to the smart instrument 10. As best seen in FIGS. 9-10, the upper enclosure half 34 has geometry that allows the forward protruding arm 80 to flex downward when depressed and to spring back to its original position when released. This allows the battery cartridge 18 to reversibly connect to the smart instrument 10.

Figure 11A:
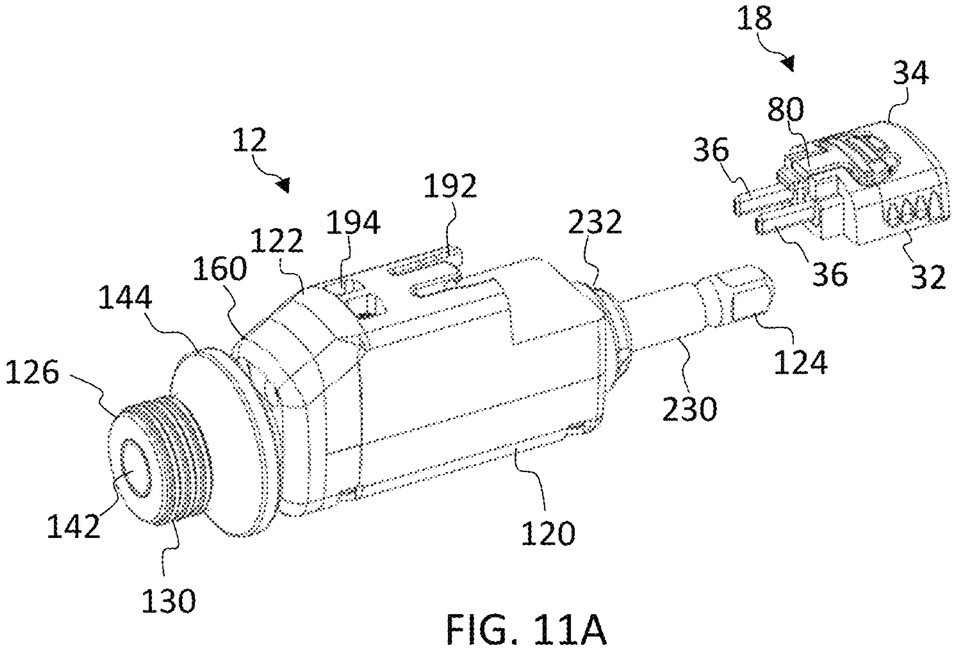
FIGS. 11A-11B show the battery cartridge being inserted into the smart instrument.
Figure 11B:
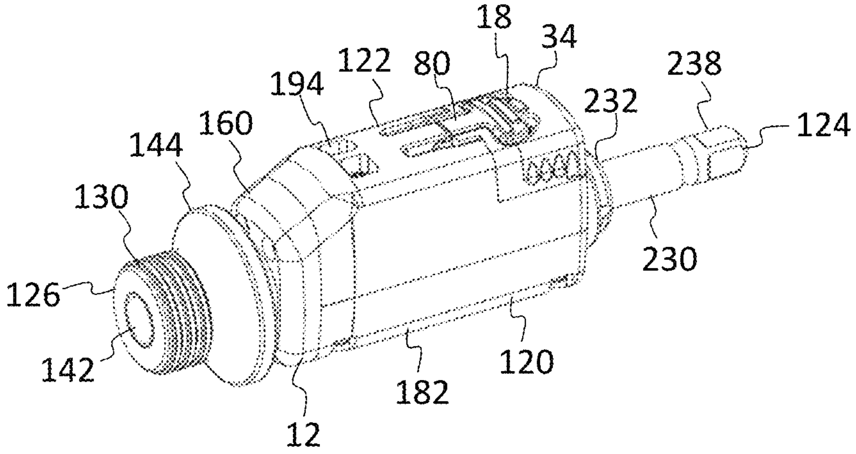
Figure 12:
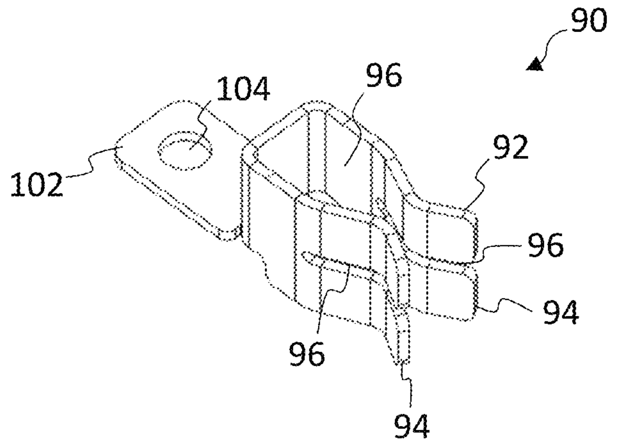
FIG. 12 shows a perspective view of the metal contact that accepts the metal blades of the battery cartridge.

FIGS. 11A-11B show the battery cartridge 18 being inserted into the adapter assembly 12. The metal blades 36 on the battery cartridge 18 independently engage with mating metal contacts 90 on the smart instrument assembly 12. As best seen in FIG. 12, the metal contact 90 may include a U-shaped body 92 terminating with ends 94, which form a receptacle 96 configured to accept the metal blade 36. The ends 94 may be bent inward toward one another and define longitudinal slits 96, which allow for increased flexibility.

Figure 13:
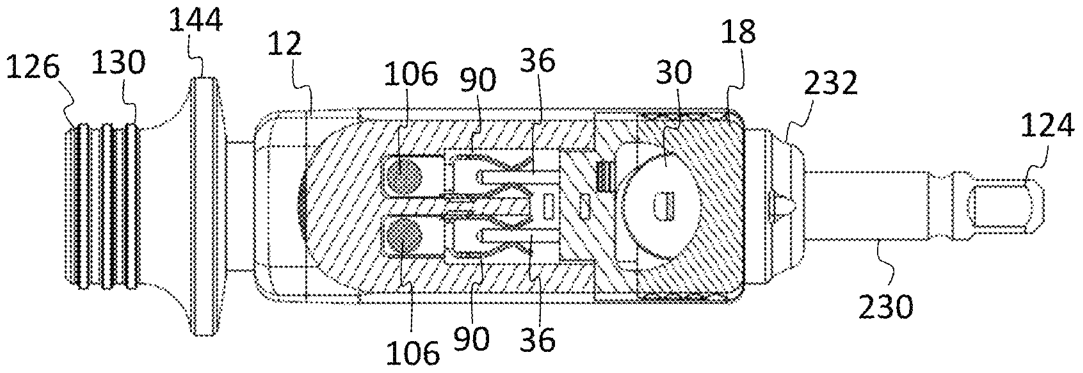
FIG. 13 shows a cross-sectional view of the battery cartridge inserted into the smart instrument assembly with the metal blades received within the metal contacts.

The U-shaped body 92 ensures the blade 36, once inserted, maintains contact along its inner surfaces. The contact 90 may include a flat tab 102 with a hole 104 for securing the contact 90 to a mounting surface of the adapter assembly 12, for example, with a bolt or screw 106. The interior of the U-shaped body 92 is dimensioned to fit the thickness and width of the metal blade 36 to ensure a secure, stable connection that minimizes the risk of disconnection or electrical resistance due to poor contact. The U-shaped body 92 may provide an inherent spring-like action, which ensures a tight grip on the inserted blade 36. The resting geometry of the metal contacts 90 is such that the distance between the two halves of the metal contact 90 is less than the width of the metal blade 36. Therefore, when the battery cartridge 18 is inserted into the smart instrument assembly 12, the metal blade 36 contacts the metal contact 90 and spreads it open. As best seen in FIG. 13, the U-shaped metal contact 90 in return applies pressure on the metal blade 36 to ensure contact is maintained.

Figure 14:
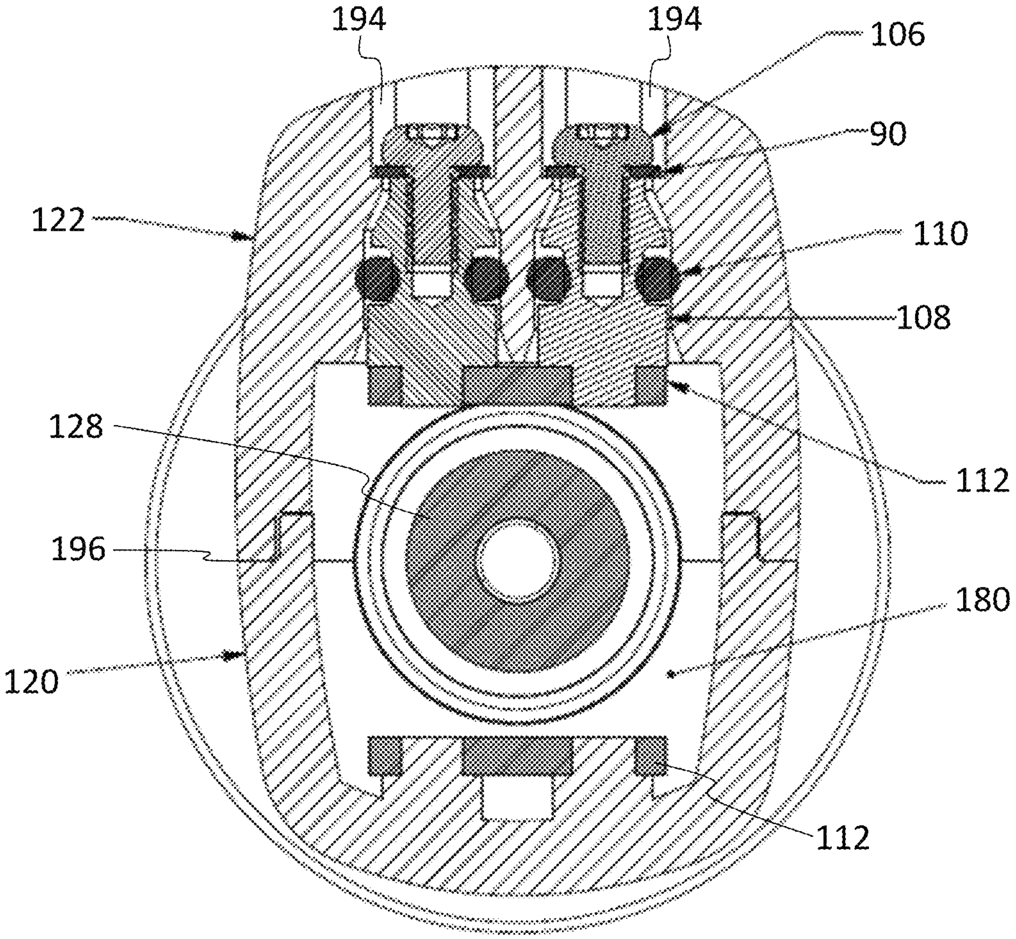
FIG. 14 is a cross-sectional view of the smart instrument assembly showing the metal contacts coupled to the printed circuit board assembly via the metal pass throughs.

The metal contacts 90 on the smart instrument assembly may be coupled to metal pass throughs 108 via threaded screws 106. As best seen in FIG. 14, the metal pass throughs 108 pass through the enclosure wall of the smart instrument assembly. O-rings 110 are positioned around the metal pass throughs 108 to prevent moisture from entering the inside of the smart instrument enclosure 120, 122. The end of the pass throughs 108 positioned inside the smart instrument enclosure 120, 122 may be coupled to a printed circuit board assembly (PCBA) 112. The PCBA may include one or more base structures or boards with electronic components mounted to the board(s), which provide electrical connectivity and enable operation of integrated circuits, sensors, and other components within an electronic system. The metal pass throughs 108 may be mounted directly to the PCBA 112 or connected to the PCBA 112 via wires. This completes the electric circuit and allows the battery 30 within the battery cartridge 18 to power the PCBA 112 located within the smart instrument assembly 10.

Force-Sensing Adapter Assembly

Turning now to FIGS. 15A-15D, the adapter assembly 12 is shown in more detail. The adapter assembly 12 is configured to sense torque and/or compression during use of the instrument 10. For example, the adapter assembly 12 may be capable of measuring axial torque and axial compression loads, thereby providing objective measurements to the user. The adapter assembly 12 includes an enclosure 120, 122, a male connection end 124, a female connection end 126, a load cell 128, printed circuit board assembly (PCBA) 112, and pass through components 108. The adapter assembly 12 is configured to secure the screwdriver shaft 20 within the female connection end 126 and engage with the handle instrument 16 at the male connection end 124. By doing so, the torque/compression sensing adapter 12 is able to measure the torque and compression exerted by the user through the full screwdriver instrument assembly 10.

Figure 15A:
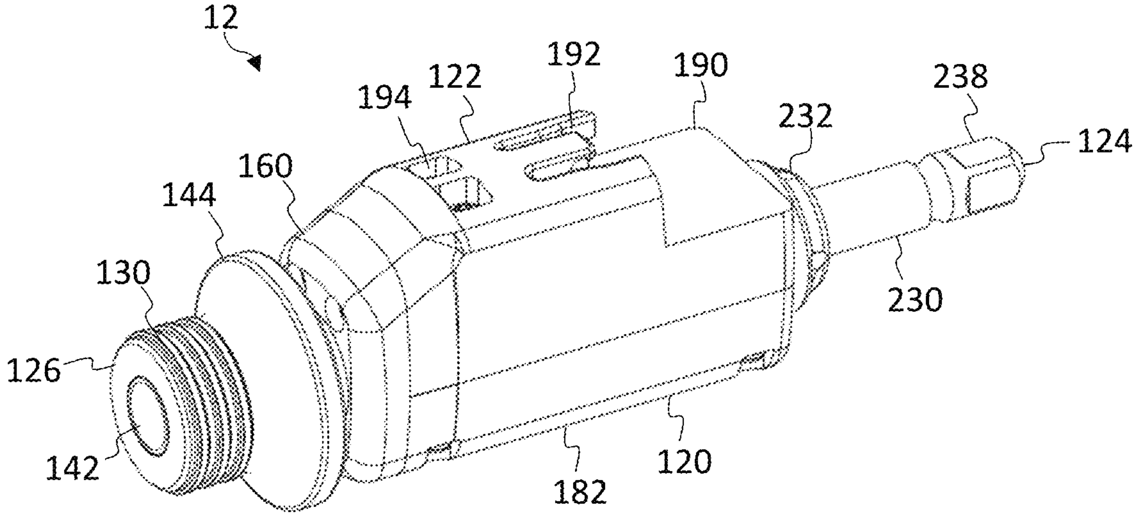
FIGS. 15A-15D show assembled and exploded views, respectively, of a torque/compression sensing adapter for the smart screwdriver assembly instrument.
Figure 15B:
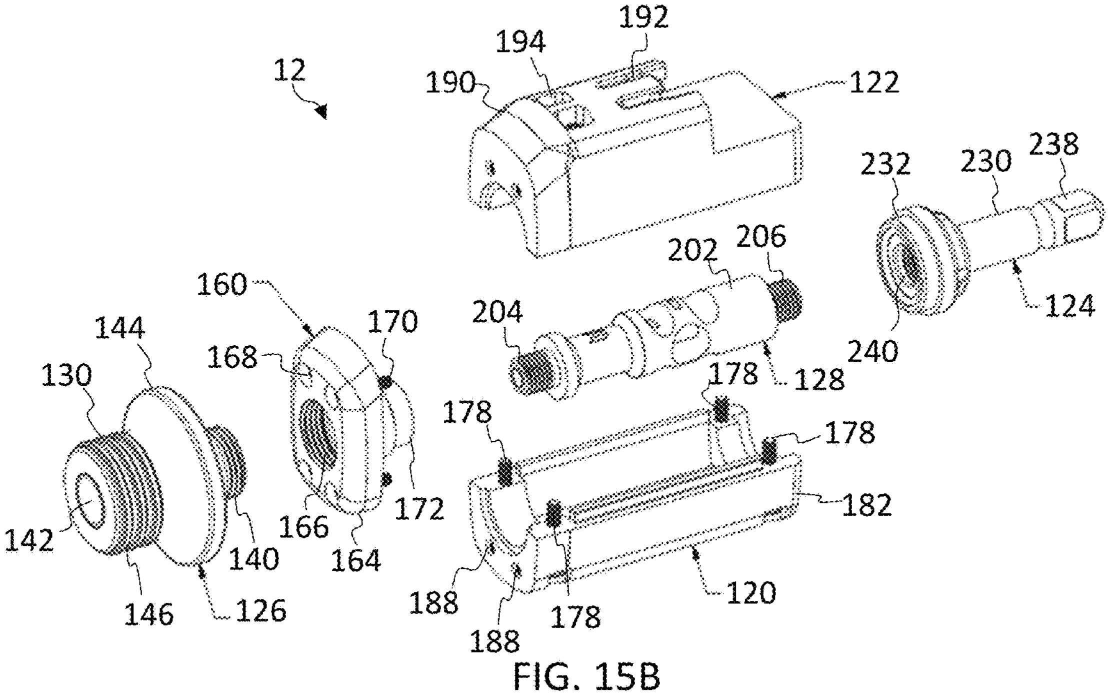
Figure 15C:
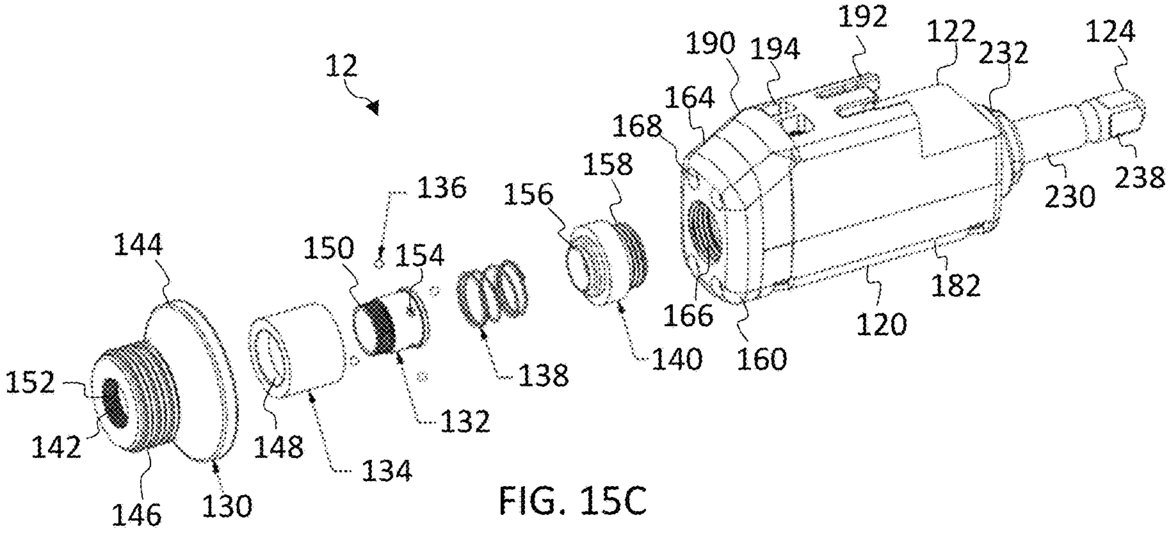
Figure 15D:
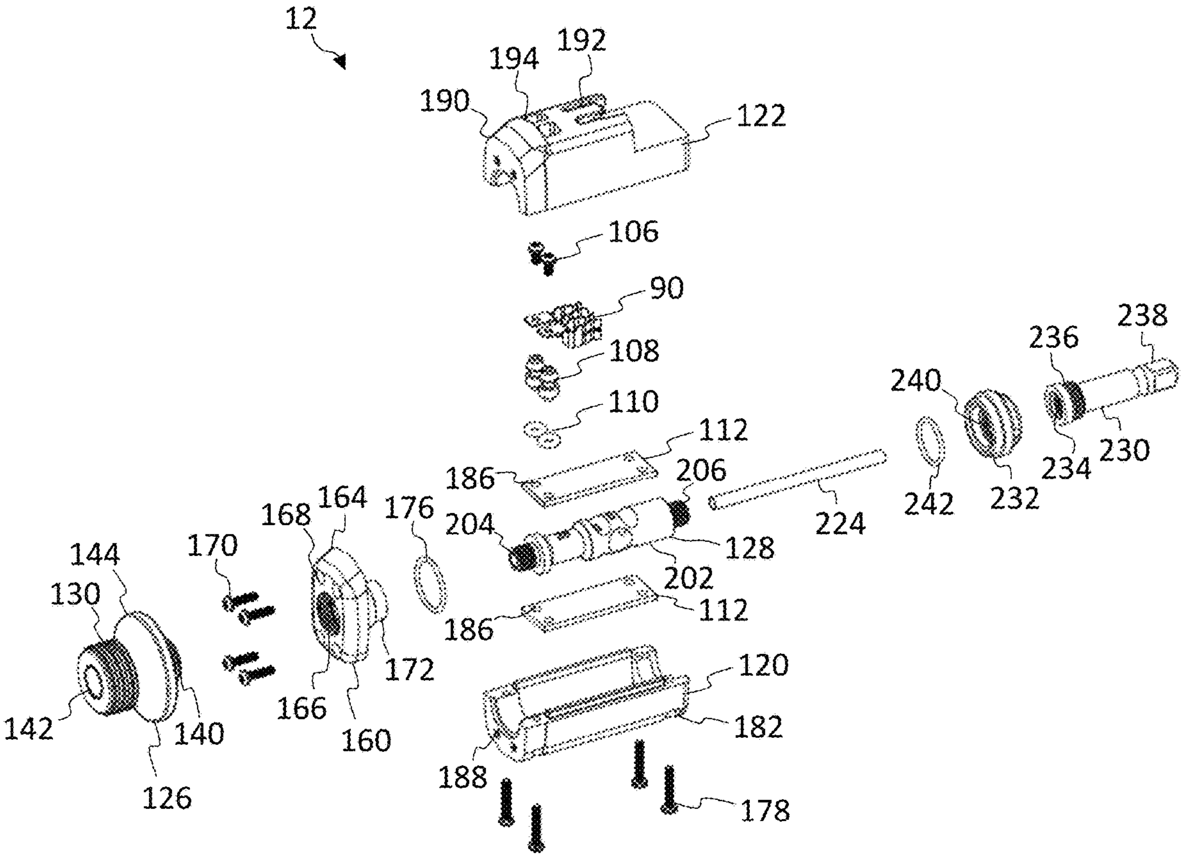

As best seen in FIG. 15C, the female connection end 126 may include a collar 130, a collet 132, a sleeve 134, ball bearings 136, a spring 138, and a driver shaft housing 140. The collar 130 includes a cylindrical outer shape with a central bore 142 sized and dimensioned to fit the collet 132, sleeve 134, and screw driver shaft 20 therein. The collar 130 may define a flange 144 and an outer threaded or textured portion 146. The sleeve 134 may include a cylindrical hollow tube, which fits inside the collar 130. The sleeve 134 defines a central bore 148 sized and dimensioned to receive the collet 132 therein. The collet 132 may include a cylindrical hollow tube, which fits inside the sleeve 134. The collet 132 defines exterior threads 150, which thread into corresponding threads 152 within the bore 142 of the collar 130. The ball bearings 136 may be positioned within cutouts or pockets 154 in the collet 132. The ball bearings 136 may be equally spaced around the periphery of the collet 132. The spring 138 may be positioned inside the sleeve 134 to bias the collet 132. The spring 138 may include a compression spring with a helical coil shape. The driver shaft housing 140 includes an attachment interface 156, which connects the driver shaft housing 140 to the end of the sleeve 134, and a threaded portion 158, which connects the driver shaft housing 140 to the face plate 160 on the enclosure 120, 122. The driver shaft housing 140 defines an inner recess 162 sized and dimensioned to receive the end of the screw driver shaft 20.

Figure 16A:
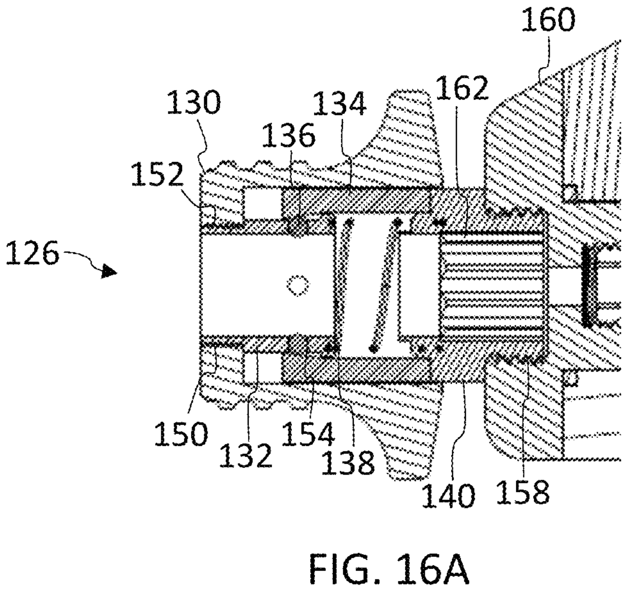
FIGS. 16A-16B show cross-sectional views of the female connection end of the torque/compression sensing adapter in the resting locked position and with the collar actuated to the unlocked position, respectively.
Figure 16B:
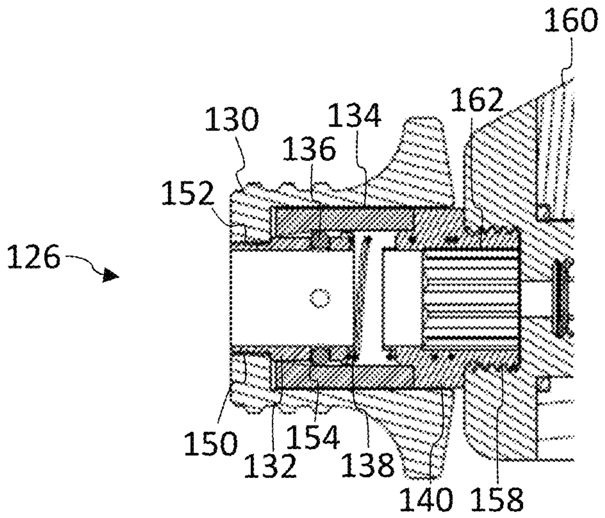

With further emphasis on FIGS. 16A-16B, the ball bearings 136 are positioned within the cutouts or pockets 154 in the collet 132 such that the ball bearings 136 can partially protrude into the inner diameter of the collet 132. As best seen in FIG. 16A, the collet 132 is positioned within the sleeve 134 such that the inner geometry of the sleeve 134 contacts the ball bearings 136 positioned in the collet 132. In this position, the female connection end 126 is in rest in the locked position. In FIG. 16B, the female connection end 126 is shown with the collar 130 actuated into the unlocked position. The collet 132 is axially aligned with the sleeve 134 but allowed to translate within the sleeve 134. The inner geometry of the sleeve 134 may be tapered allowing the ball bearings 136 to translate within the pockets 154 in the collet 132 to a degree dictated by the position of the collet 132 within the sleeve 134. At rest, the spring 138 forces the collet 132 to the distal end of the sleeve 134 where the smaller end of the taper is located, thus forcing the ball bearings 136 into the bottom of the pockets 154 in the collet 132 causing them to protrude into the inner diameter of the collet 132. The collar 130 is coupled to the collet 132 such that the user may actuate the collar 130 and translate the collet 132 to the proximal end of the sleeve 134, compressing the spring 138. The inner diameter of the sleeve 134 at the proximal portion may be larger allowing the ball bearings 136 to translate higher in the pockets 154, thus decreasing the distance that they protrude into the inner diameter of the collet 132 (e.g., FIG. 16B).

Figure 17A:
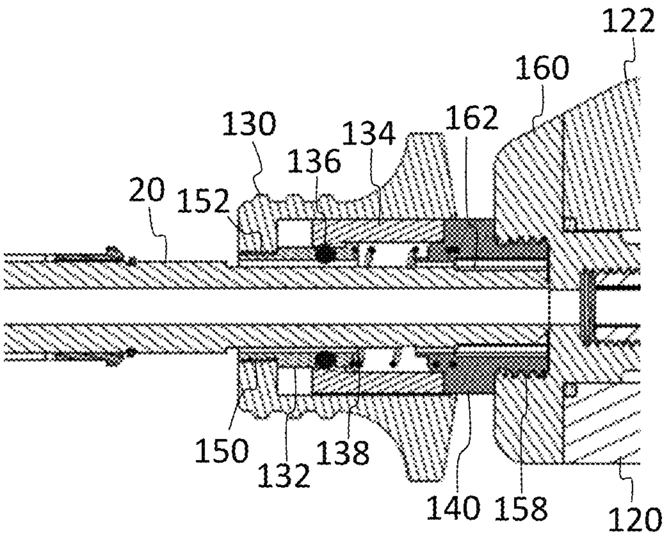
FIGS. 17A-17B show cross-sectional views of the screwdriver shaft engaged with the adapter assembly.
Figure 17B:
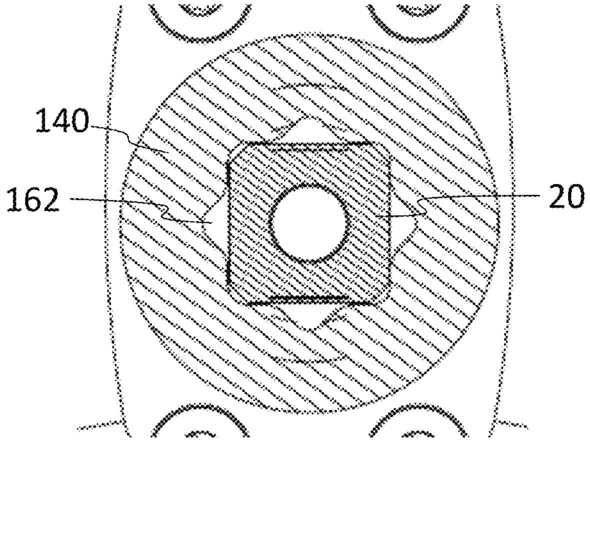
Figure 18:
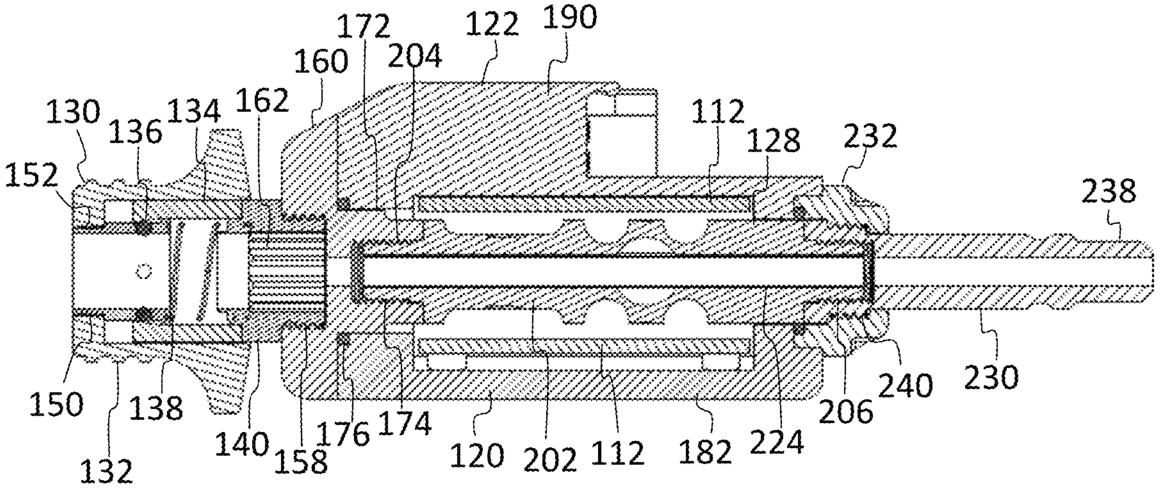
FIG. 18 shows a cross-sectional view of the fully assembled adapter assembly.

To connect the screw driver shaft 20 to the adapter assembly 12, the screw driver shaft 20 is insertable into the female connection end 126 through the collar 130 and into the recess 162 in the driver shaft housing 140. As best seen in the cross-sectional views of FIGS. 17A-17B, the screw driver shaft 20 is engaged with the adapter assembly 12 by positioning the proximal end of shaft 20 through the collar 130, collet 132, and sleeve 134, and into the driver shaft housing 140. The recess 162 in the driver shaft housing 140 has geometry, such as an eight-lobe, hex shape, or square shape, to engage with mating geometry on the proximal end of a screwdriver shaft 20. For example, an eight-lobe recess 162 may receive a square shaped driver shaft 20, thereby keying the parts together. The mating geometry allows the adapter assembly 12 to exert torque/compression on the screw driver shaft 20 when in use.

Figure 19:
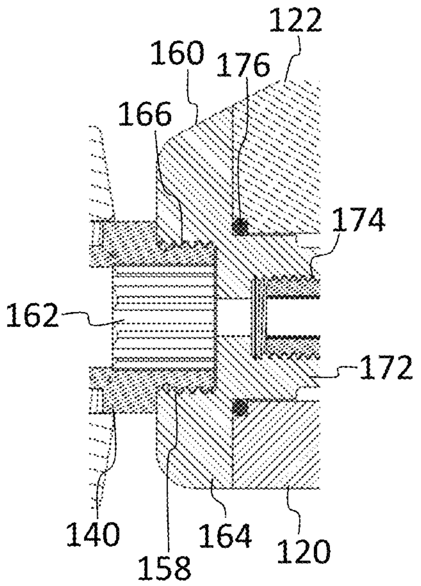
FIG. 19 shows a close-up cross-sectional view of the assembly with the O-ring between the face plate and enclosure.
Figure 20:
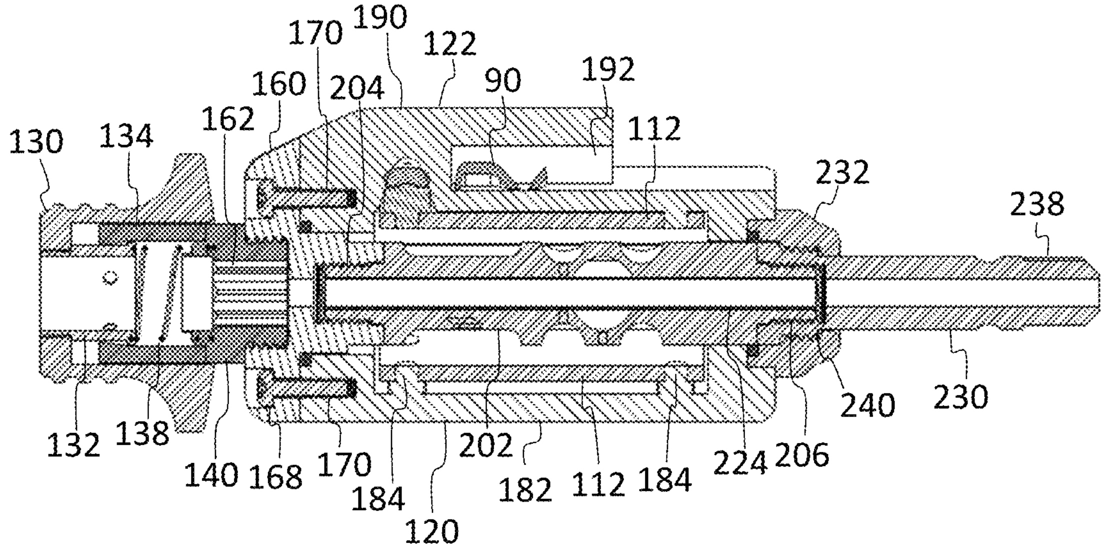
FIG. 20 shows a cross-section view of the face plate attached to the enclosure with assembly screws.

With further emphasis on FIGS. 19-20, the female connection portion 126 may be coupled to the load cell 128 and enclosure 120, 122 via the face plate 160. The face plate 160 may include a plate 164 with contoured edges defining a central opening or recess 166 which may be threaded to secure the threaded end 158 of the driver shaft housing 140 to the face plate 160. Around the perimeter of the plate 164, mounting holes 168 may be configured to receive assembly screws, bolts, or other fasteners 170. For example, four assembly screws 170 may secure the face plate 160 to the enclosure 120, 122. As best seen in FIG. 19, an O-ring 176 may be positioned between the face plate 160 and enclosure halves 120, 122 to create a seal, preventing moisture from entering into the interior of the enclosure 120, 122. The face plate 160 may include a cylindrical boss 172 extending from the plate 164, which ensures the face plate 160 is aligned with the enclosure 120, 122 and load cell 128. The boss 172 defines an opening or recess 174, which may be threaded to engage with the end of the load cell 128, thereby securely attaching the load cell 128 to the face plate 160.

Figure 21:
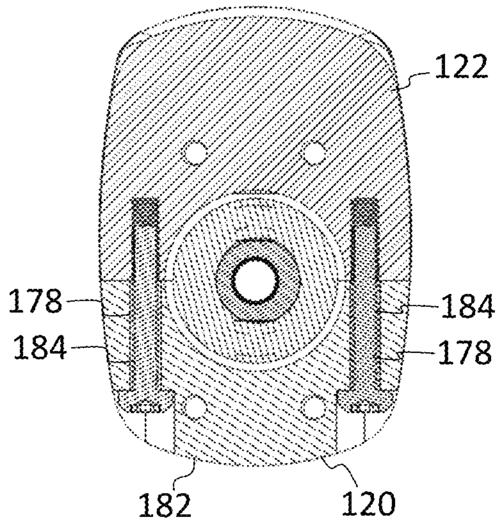
FIG. 21 shows a cross-sectional view of the enclosure halves secured together by assembly screws.

With further emphasis on FIG. 21, the enclosure 120, 122 is split into two halves, which may be secured together with screws, bolts, or other fasteners 178. For example, four threaded screws 178 may be used to secure the enclosure pieces 120, 122 together. The two halves of the enclosure 120, 122 create a sealed cavity 180 on the interior that protects the electronic components from moisture. The lower enclosure half 120 may have a rectangular body 182 with a U-shaped cross-section to house the components therein. The lower enclosure half 120 may be configured to secure the lower PCBA 112 inside the enclosure 120, 122. The lower enclosure 120 may be configured to integrate seamlessly with the lower PCBA. For example, The lower enclosure half 122 may have bosses 184 that fit into corresponding through holes 186 on the lower PCBA 112. The bosses 184 may include cylindrical or tapered protrusions, which align and secure the PCBA to the lower enclosure 120. The lower enclosure 120 may include blind holes and/or through openings 188, which act as mounting points for securing the lower half 120 to the upper counterpart 122 and the face plate 160 to the full enclosure 120, 122.

Figure 22:
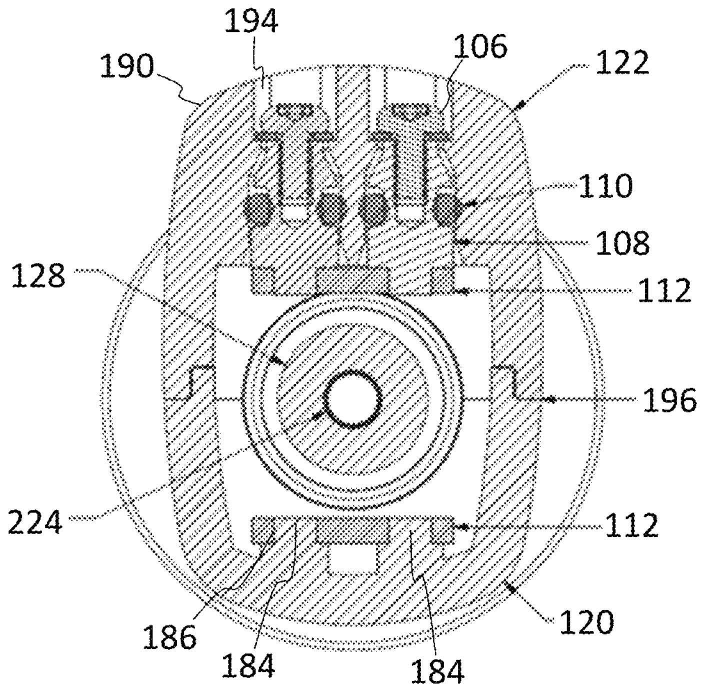
FIG. 22 shows a cross-sectional view of the assembly with the metal pass throughs mounted to the printed circuit board assembly.

The upper enclosure half 122 may have a complementary rectangular body 190 with a U-shaped cross-section. The upper enclosure half 122 may be configured to mate with the battery cartridge 18. In particular, a battery recess 192 defined along an outer surface of the upper enclosure 122 may define a plug shaped recess sized and dimensioned to receive the battery cartridge 18. A wall of the battery recess 192 may include a notch 244 configured to receive the arm 80 of battery cartridge 18 to secure the battery cartridge 18 in the battery recess 192. The upper enclosure half 122 defines channels 194 configured for receiving the electrical components. As best seen in FIG. 22, the metal contacts 90 and metal pass throughs 108 are secured within the upper enclosure half 122. O-rings 110 are positioned around the metal pass throughs 108 to seal the enclosure cavity 180. The upper enclosure half 122 may be configured to secure the upper PCBA 112 inside the enclosure 120, 122. The upper PCBA 112 may be directly mounted to the metal pass throughs 108 or connected via wires.

Figure 23:
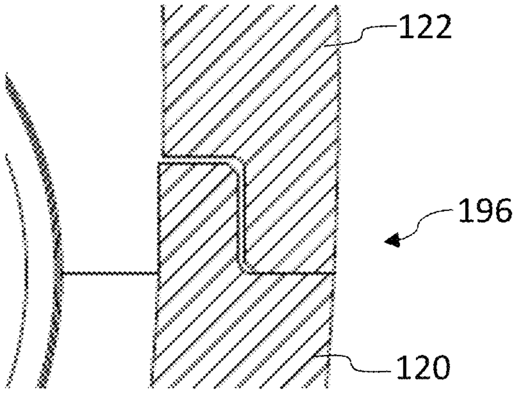
FIG. 23 shows a close-up view of the seam between the two enclosure halves.

As best seen in FIG. 23, the upper and lower enclosure halves 120, 122 may have geometry along their borders to create a seam 196. The seam 196 may have an edge or lip with a stepped geometry, for example, around the perimeter to create a moisture-resistant environment. The seam 196 may be sealed during assembly in order to prevent moisture from entering the interior 180 of the enclosure 120, 122. The seam 196 may be sealed by epoxy, ultrasonic welding, or other techniques. Alternatively, the interior cavity 180 of the enclosure 120, 122 may be potted with silicone or a similar material to protect the electronics from moisture.

Figure 24:
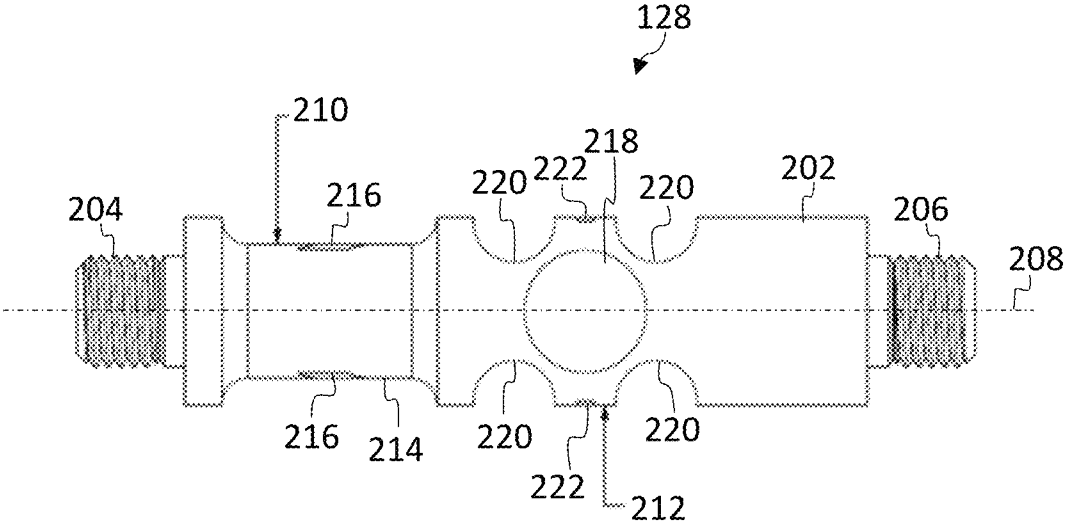
FIG. 24 shows a torque and compression sensing load cell for the smart screwdriver assembly instrument.

Turning now to FIG. 24, the load cell 128 is coupled directly to the face plate 160 and is positioned inside the sealed space 180 created by the enclosure halves 120, 122. The main body 202 of the load cell 128 may be cylindrical or beam-shaped, designed to handle mechanical load. The load cell 128 may be composed of a high-strength metal such as steel or aluminum, which can accurately measure force without permanent deformation. Each end of the load cell 128 may have a threaded section 204, 206 or other connector interface for attachment to the face plate 160 and cap 232 of the male connector 124, respectively. The load cell 128 is configured to measure force applied directly or indirectly including tension, compression, or both.

Figure 25A:
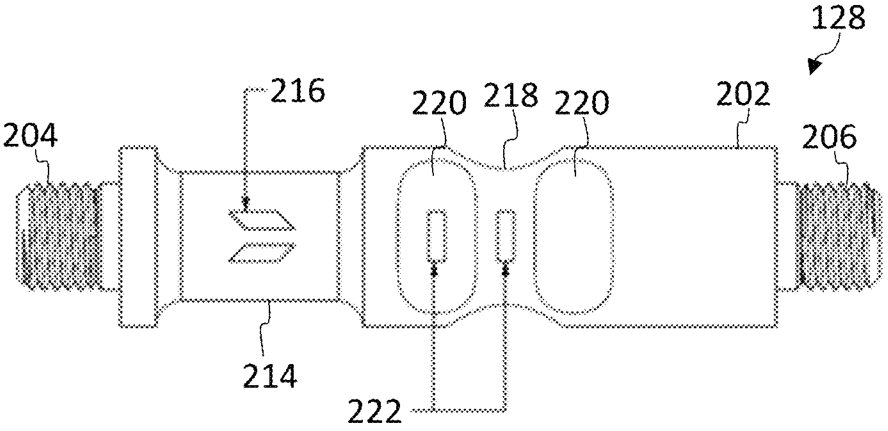
FIGS. 25A-25C show strain gages positioned on the load cell, a cross-sectional view of the load cell showing the thin walled tube, and a perspective view of the load cell with the thin walled tube.

The load cell 128 may have a torque sensing portion 210 and a compression sensing portion 212 with sensors or gages that detect force. For example, the torque sensing portion 210 may include an area of decreased diameter 214 with strain gages 216 mounted to the outer surface. This area experiences deflection when torque is applied to the load cell 128, which is sensed by the strain gages 216. The compression sensing portion 212 may include a through hole 218 cut transversely through a long axis 208 of the part and/or relief cuts 220 positioned symmetrically around the through hole 218. The through hole 218 may be cylindrical in shape and the relief cuts 220 may be semi-spherical, elliptical or another suitable contour to provide flexibility to the load cell 128. Strain gages 222 are mounted on the outer surface between and within the relief cuts 220. Strain gages 222 may also be placed within the through hole 218 of the compression sensing portion 212. This area experiences deflection when compression is applied to the load cell 128, which is sensed by the strain gages 222. FIG. 25A shows placement for strain gages 216, 222 although it will be appreciated that any suitable placement and configuration may be selected.

Figure 25B:
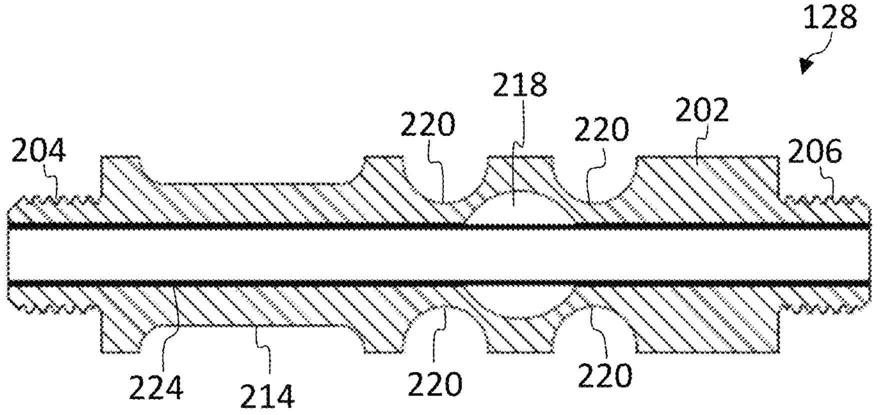
Figure 25C:
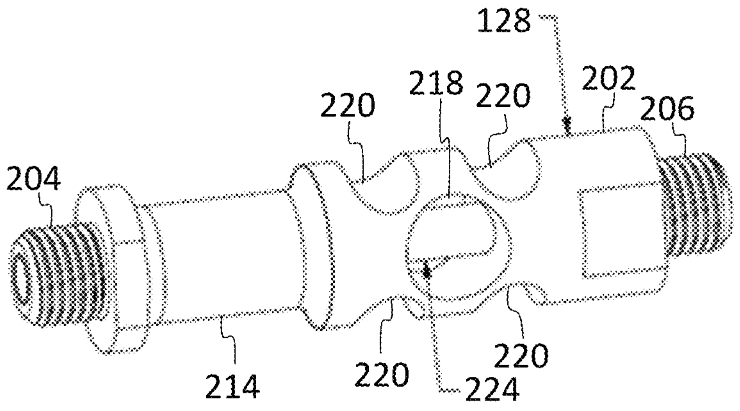

With further emphasis on FIGS. 25B-25C, the load cell 128 may be cannulated to allow the instrument to be used with K-wires. A thin walled metal tube 224 may be positioned within the inner cannulation of the load cell 128 and welded at both ends to seal the inside cavity of the enclosure from moisture. The tube 224 may be pliable enough to allow the necessary deformation in the load cell 128 to measure torque and compression intraoperatively. Alternatively, the inner tube 224 may be composed of silicone or other similar malleable material in order to seal off the inside of the smart instrument enclosure from the outside environment.

The strain gages 216, 222 may be connected to the PCBA 112 via wires such that the signals from the strain gages 216, 222 may be received and processed by the PCBA 112. The PCBA 112 is powered by the battery cartridge 18 and may have an antenna to wirelessly transmit the signals received by the strain gages 216, 222. The signals from the strain gages 216, 222 may be processed and information may then be sent, for example, via radiofrequency (RF) communication (Bluetooth, Wi-Fi, Zigbee, etc.) or other suitable communication to an external communication receiver. The upper and lower enclosure halves 120, 122 may be composed of plastic or other RF compatible material to allow the antennae on the PCBA 112 to send signals from the device. Alternatively, the adapter assembly 12 could be wired directly to the receiver.

The PCBA 112 may be connected to LED lights that can be seen by the user. The LED lights may communicate information about the state of the instrument or information about the torque and compression data sensed by the instrument 10. For example, the LED may light up green when the battery is full and red when the battery is low. Or the LED light could light up blue when torque is sensed; the intensity of the light may vary according to the amount of torque sensed by the instrument 10.

Figure 26A:
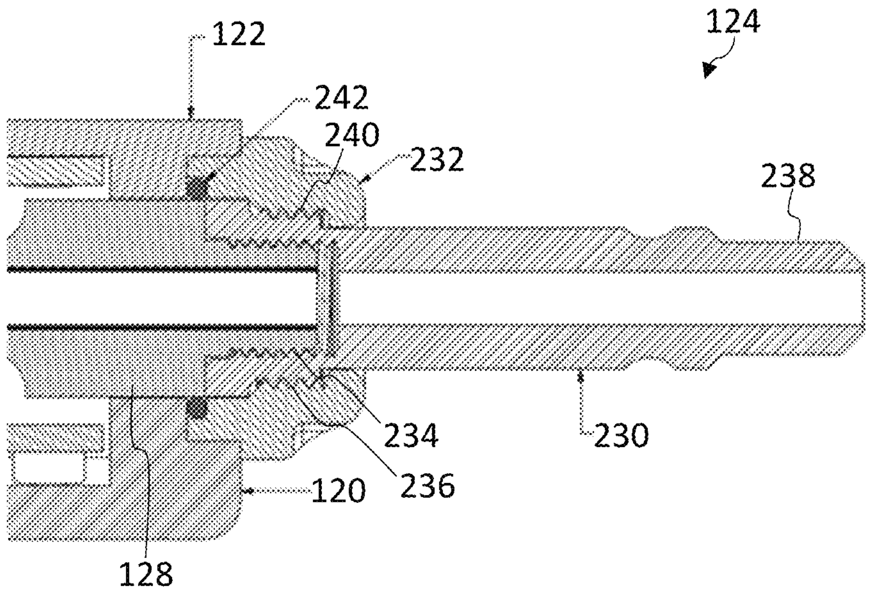
FIGS. 26A-26B show cross-sectional views of the male connection end with the threaded cap and O-ring, and showing the battery cartridge assembled to the smart instrument.
Figure 26B:
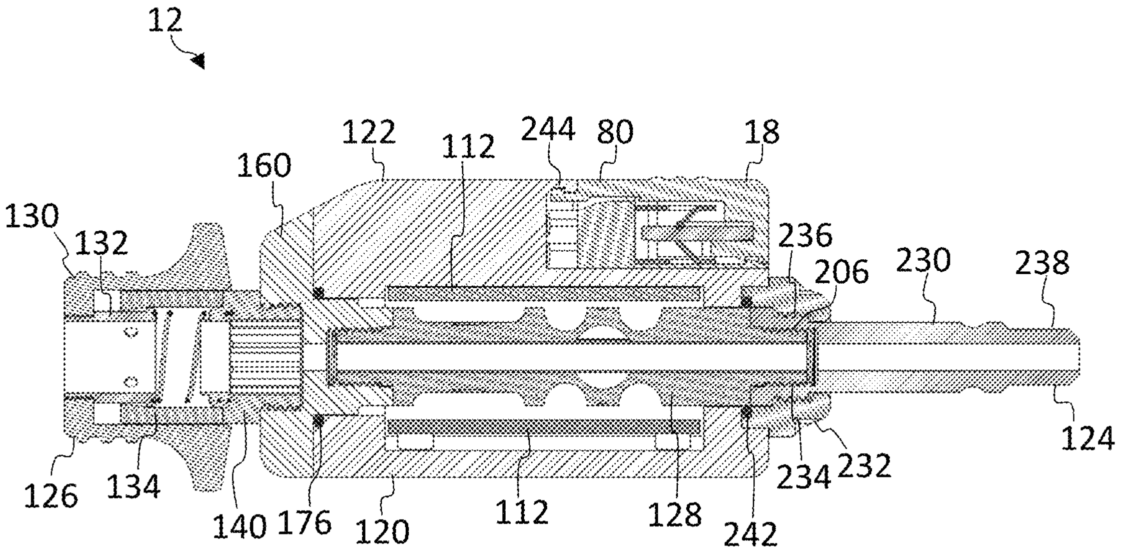

Turning now to FIGS. 26A-26B, the load cell 128 is coupled directly to the male connection end 124. As a result, when force or torque is applied to the male connection end 124 by the user through handle 16 attached to the instrument 10, the force and torque is transmitted directly through the load cell 128. The strain gages 216, 222 on the load cell 128 consequently sense the deflection in the load cell 128 caused by the exerted force and/or torque and send the signals to the PCBA 112 which processes the signals and sends the information wirelessly to an external receiver. The force and/or torque is also transferred to the female connection end 126 which then transfers it to the screwdriver or other instrument attached to the adapter assembly 12. In this manner, the instrument 10 is able to communicate to the surgeon how much force and/or torque is exerted during screw insertion or other parts of the procedure, which help the surgeon make more informed decisions.

The male connection end 124 includes a shaft 230, which attaches to the load cell 128. The adapter assembly 12 may also contain a threaded cap 232 that is coupled to the male connection end 124 and butts up against the enclosure 120, 122. The shaft 230 may be cannulated with an internal threaded portion 234 configured to mate with corresponding threads 206 on the load cell 128. The shaft 230 may also include an external threaded portion 236 which mates with corresponding threads 240 inside the threaded cap 232. The shaft 230 extends to a free end with an attachment interface 238 with a geometry configured to couple the shaft 230 to the handle 16. The attachment interface 238 may include a quick connection to the handle 16, for example. The threaded cap 232 includes a cylindrical body with a through bore that is at least partially threaded 240 and interfaces with the outer threads 236 of the shaft 230. The threaded cap 232 nests within the end of the enclosure 120, 122. For example, a reduced diameter portion of the threaded cap 232 can fit within a corresponding recess in the enclosure 120, 122. As best seen in FIG. 26A, an O-ring 242 may be positioned between the threaded cap 232 and the enclosure 120, 122 to prevent moisture from entering the interior of the enclosure 120, 122.

Figure 27:
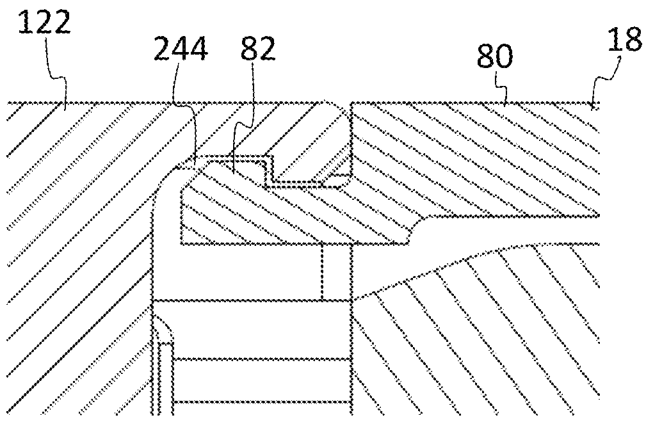
FIG. 27 shows a close-up view of the arm of the battery cartridge engaging the smart instrument assembly.
Figure 28:
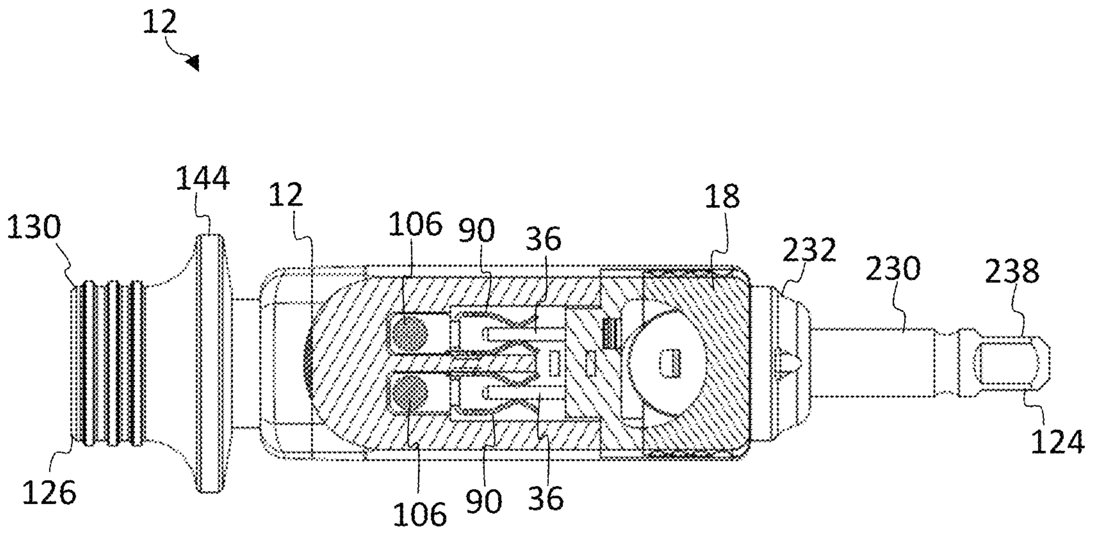
FIG. 28 shows a cross-section view of the battery cartridge inserted into the smart instrument assembly with the metal blades contacting the metal contacts.

FIG. 26B shows a cross-sectional view of the entire adapter assembly 12 including the enclosure 120, 122, the male connection end 124, the female connection end 126, and the load cell 128. In this view, the battery cartridge 18 is also assembled to the smart instrument 10. The upper enclosure half 122 includes recess 192, which mates with the battery cartridge 18 such that the battery cartridge 18 is securely coupled to the adapter instrument when inserted. As best seen in FIG. 27, the hook 82 of the arm 80 on the battery cartridge 18 is receivable within notch 244 in the upper enclosure 122, thereby securing the battery cartridge 18 to the instrument 10. The arm 80 is able to flex downward when depressed and can spring back to its original position when released. This allows the battery cartridge 18 to reversibly connect to enclosure 120, 122. The user aligns and inserts the battery cartridge 18 into the battery recess 192 on the torque/compression sensing adapter 12, engaging the metal blades 36 on the battery cartridge 18 with the metal contacts 90 in the adapter assembly 12. As best seen in FIG. 28, contact between the metal blades 36 in the battery cartridge 18 and the metal contacts 90 in adapter assembly 12 completes the electric circuit and provides power to the PCBA 112.

Figure 29:
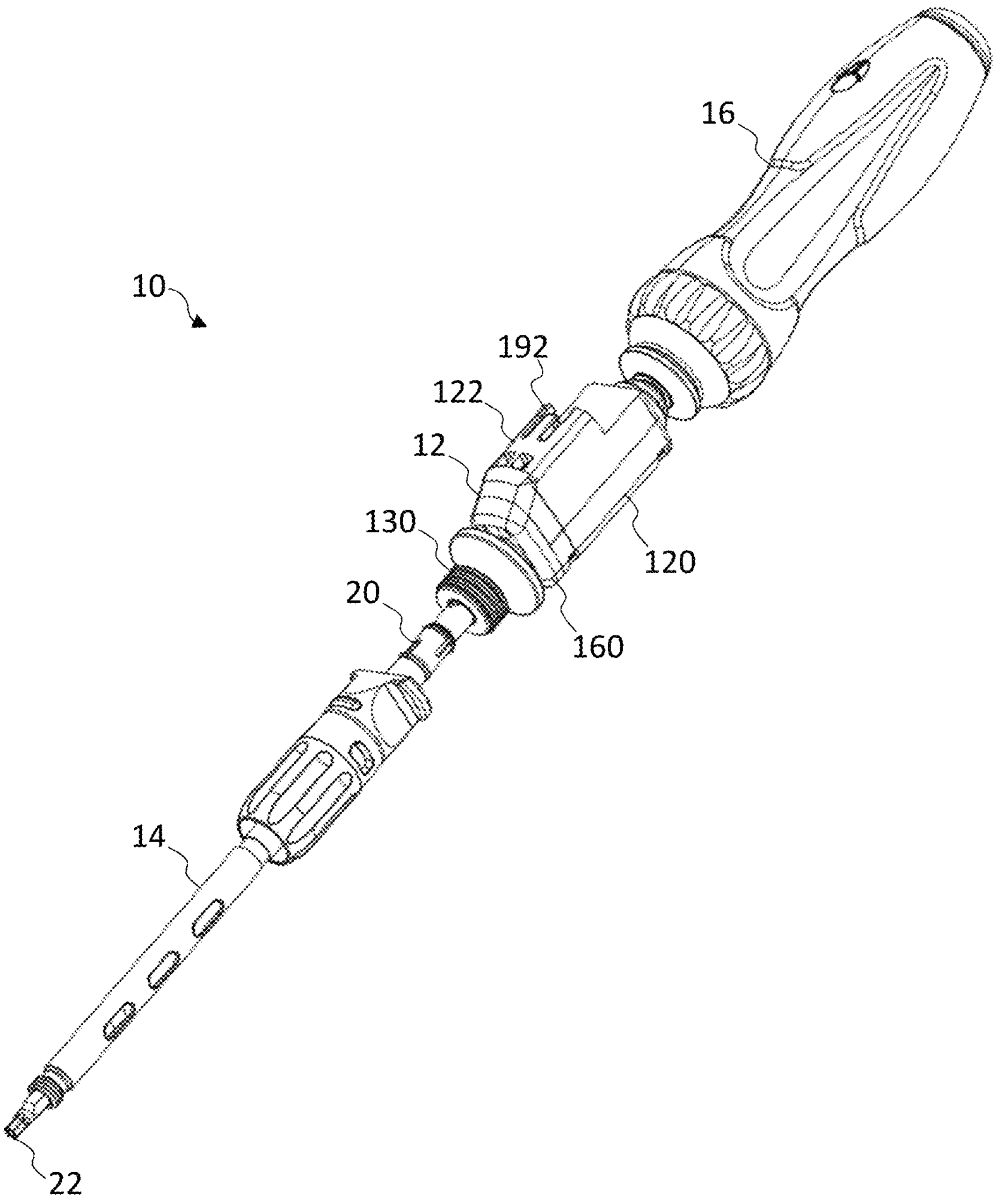
FIG. 29 shows the smart screwdriver instrument assembly for measuring torque and compression loads with the battery omitted according to one embodiment.

FIG. 29 provides an example of the full screwdriver instrument assembly 10 with the battery cartridge 18 omitted from battery recess 192. The adapter assembly 12 is configured to sense and measure torque and compression loads exerted by the user through the instrument 10. The screw driver shaft 20 connects with the adapter assembly 12, which, upon the user applying force or torque to the handle 14, transmits this force to the screw driver shaft 20. This setup not only facilitates the insertion of the implant but also allows the adapter assembly 12 to measure and relay the torque and force applied during the procedure back to the user for optimal control and feedback.

Intraoperative Communication Dongle

Figure 30A:
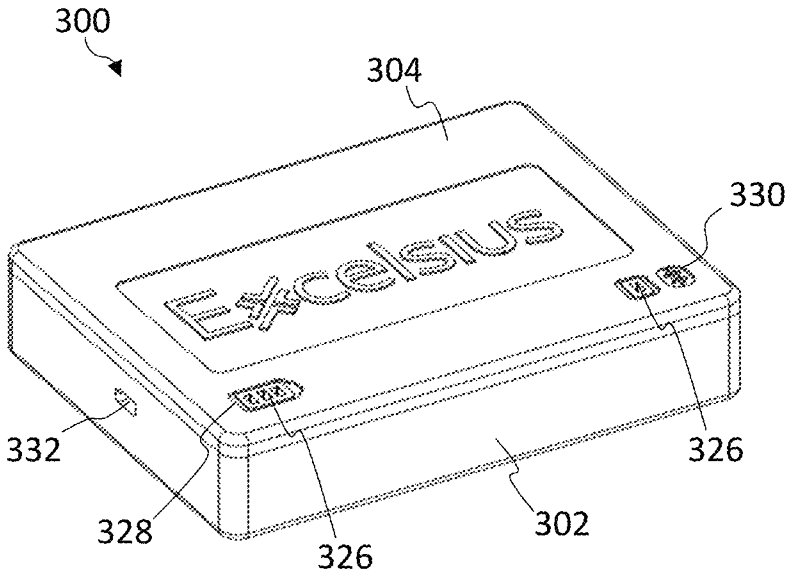
FIGS. 30A-30B show a communication dongle and enclosure according to one embodiment.
Figure 30B:
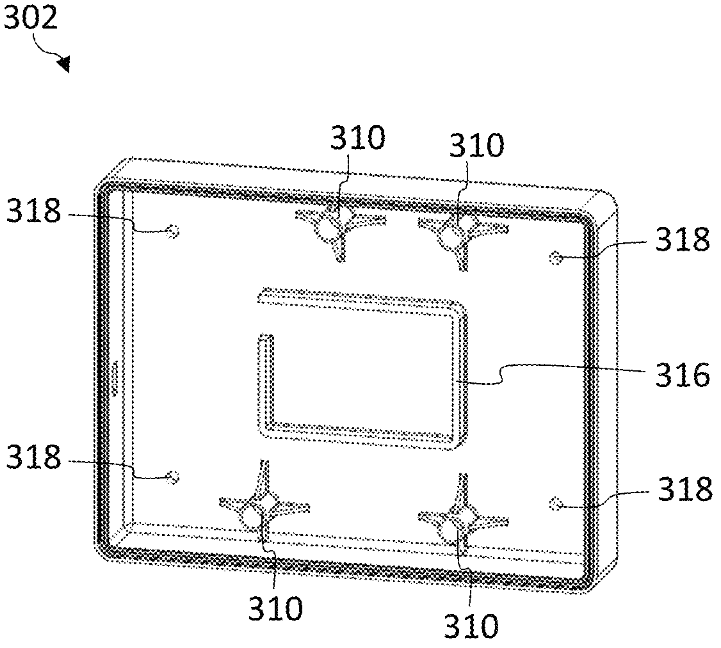

Turning now to FIGS. 30A-30B, a communication dongle 300 is shown according to one embodiment. The communication dongle 300 is configured to receive signals transmitted by the torque/compression sensing adapter instrument 10 described above. The dongle 300 captures signals from the adapter 12, such as the torque applied to the instrument, and transmits this information to a computer or other suitable system. The computer then provides these values to the user, providing real-time feedback to the surgeon.

Figure 31A:
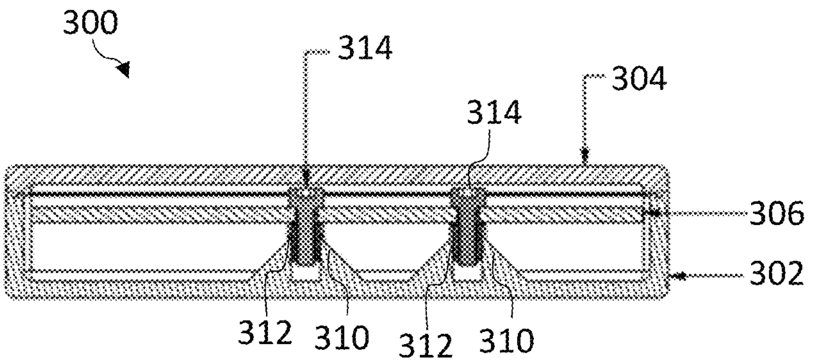
FIGS. 31A-31C show cross-sectional views of the communication dongle including a printed circuit board assembly secured to the enclosure, a battery positioned within the enclosure, and rubber feet secured to the enclosure.
Figure 31B:
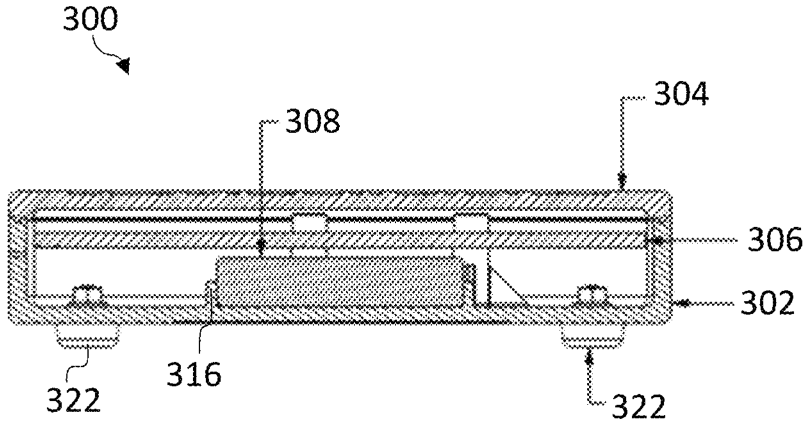
Figure 31C:
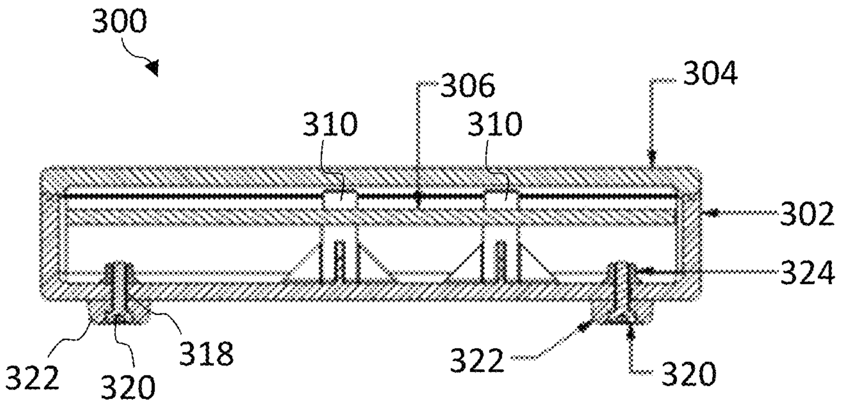

The communication dongle 300 may include an enclosure 302, enclosure lid 304, PCBA 306, battery 308, and a connector cable 309 (e.g., USB cable) to enable data transfer and power supply. The enclosure 302 may have a generally rectangular shape for holding the PCBA 306 and battery 308. As best seen in FIG. 30B, the enclosure 302 may have four posts 310 to mount the PCBA 306. With further reference to FIG. 31A, each mounting post 310 may include a raised portion on the inside of the enclosure 302 with a thread insert 312 for engagement with a threaded assembly screw 314. The PCBA 306 may include mounting holes that are configured to line up with the posts 310 in the enclosure 302. The assembly screws 314 are inserted through the holes in the PCBA 306 and threaded into the posts 310 to fasten the PCBA 306 to the enclosure 302. With further reference to FIG. 31B, the enclosure 302 may include a raised wall 316 configured to hold the battery 308, such as a coin cell battery or rechargeable battery. The battery 308 may be positioned beneath the PCBA 306 and connected via wires. Alternatively, the battery 308 could be mounted directly to the PCBA 306. With further reference to FIG. 31C, the enclosure 302 may include through holes 318 configured to accept threaded fasteners 320 to secure feet 322. Rubber feet 322 with through holes to accept the fasteners 320 are positioned beneath each through hole 318 in the enclosure 302 and are secured with nuts 324. The rubber feet 322 provide contact points for the enclosure 302 to rest on different surfaces.

Figure 32:
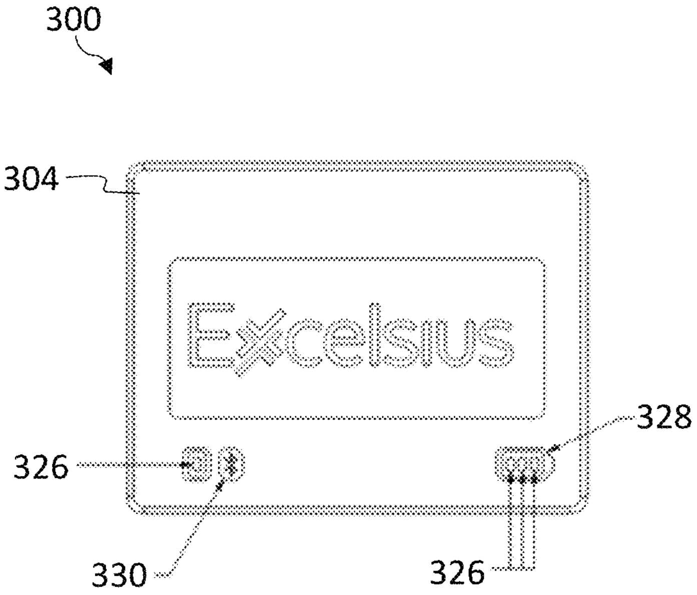
FIG. 32 shows the enclosure lid positioned above LED lights on the printed circuit board assembly to communicate information to the user.

Turning now to FIG. 32, the PCBA 306 may have LED lights 326 that are positioned under specific features on the enclosure lid 304 such that they communicate information to the user. For example, LED lights 326 on the PCBA 306 may be positioned beneath a window on the enclosure lid 304 in the shape of a battery icon 328. The LED lights 326 in this area may be programmed to communicate information about the current battery level of the device to the user. The number, color, and/or state (e.g., solid vs. flashing vs. off) of LED lights illuminated in this area could signal how much battery life is remaining in the device or battery charging status of the device 300. A different area of the enclosure lid 304 may have a symbol 330, for example, in the shape of a Bluetooth symbol. The LED light 326 in this area may be used to communicate information to the user about the connection status of the device with other communication dongles or with the computer (which may be integrated with a surgical robot). The number, color and/or state may signal whether or not the device is connected and successfully communicating with the computer, or if the device is attempting to establish a connection.

A port 332, such as a Universal Serial Bus (USB) port, may connect the dongle 300 to an external device, for example, for data transfer and/or to a power source for power connection. The port 332 may connect a cable, such as a USB cable 309, for high-speed data transfer and/or power supply. The PCBA 306 may also have an antenna to transmit and receive RF communication signals from smart surgical instruments, such as smart screwdriver instrument 10. The communication dongle 300 may transmit and receive signals, for example, via Bluetooth, Wi-Fi, Zigbee, or other RF communication protocol. The dongle 300 may transmit signals to a computer, which may use the information to perform various functions. For example, the communication dongle 300 may receive information from the torque/compression sensing adapter 12, such as the amount of torque placed on the instrument 10. This information could then be transmitted from the communication dongle 300 to a computer which then displays the torque value on a graphical user interface to the surgeon. It will be appreciated that any suitable information may be transmitted and conveyed based on the type of instrument being used.

Figure 33:
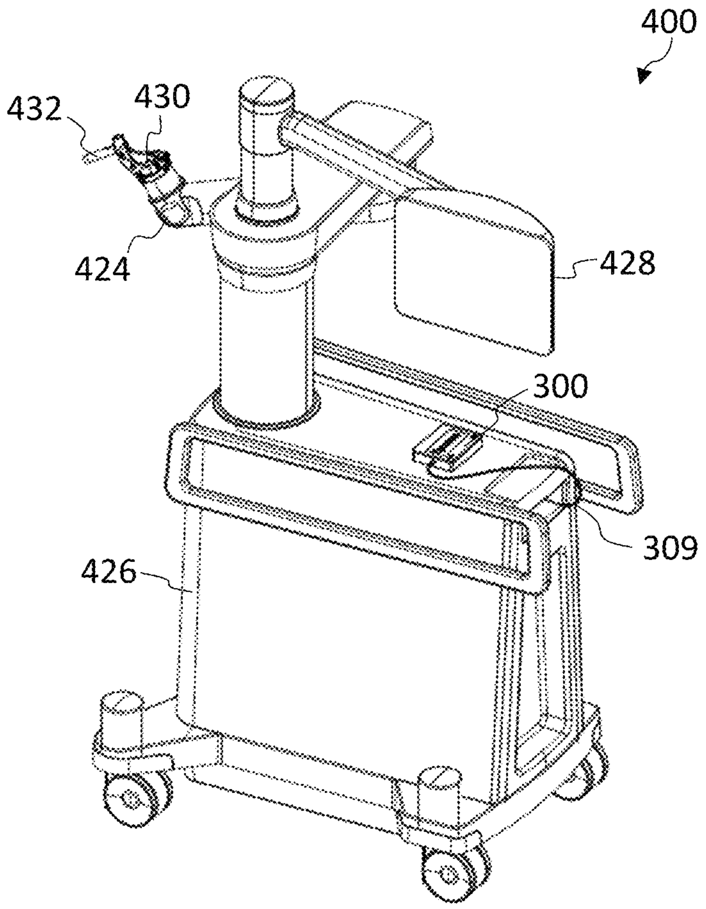
FIG. 33 shows a communication dongle connected to a surgical robot according to one embodiment.

The computer receiving the information from the communication dongle 300 may be integrated into a surgical robot, such as surgical robotic and navigation system 400 shown in FIG. 33. The surgical robot system 400 may include, for example, one or more robot arms 424, a base 426 with one or more computers having a processor, programming, and memory, a display or monitor 428 (or optional wireless tablet) electronically coupled to the computer, and an end-effector 430, for example, including a guide tube 432 electronically coupled to the computer and movable based on commands processed by the computer.

The on-board computer may include a central processing unit (CPU), memory, and an input/output interface. The central processing unit carries out the instructions of a computer program or software by performing arithmetical, logical, control, and input/output (I/O) operations specified by the instructions. The memory may include volatile and non-volatile memory storage that temporarily or permanently store data and instructions that are currently in use or will be needed by the central processing unit. This may include, for example, random access memory (RAM), read-only memory (ROM), and storage devices like hard drives. It will be appreciated that tangible/non-transitory computer-readable medium comprising software code or storing instructions executable by one or more processors may be adapted, when executed on a data processing apparatus, to perform any computer method set out herein. The input/output interface allows the computer system to interact with the user, take in information, and deliver results, and may include devices such as a monitor, keyboard, mouse, network interface for internet connectivity, and so forth. Although an on-board computer is exemplified herein, it will be appreciated that the computer or one or more functions may be replaced or supplemented with external devices or systems (e.g., cloud computing).

The surgical robot system 400 may also utilize a camera, for example, positioned on a separate camera stand. The camera may include any suitable camera or cameras, such as one or more infrared cameras (e.g., bifocal or stereophotogrammetric cameras), able to identify, for example, active and passive tracking markers in a given measurement volume viewable from the perspective of the camera. The camera may scan the given measurement volume and detect the light that comes from the markers in order to identify and determine the position of the markers in three-dimensions. For example, passive markers may include retro-reflective markers that reflect infrared light (e.g., they reflect incoming IR radiation into the direction of the incoming light), for example, emitted by illuminators on the camera or another suitable device. Further examples of surgical robotic and/or navigation systems can be found, for example, in U.S. Pat. Nos. 10,675,094 and 9,782,229, which are incorporated by reference herein in their entireties for all purposes.

The communication dongle 300 may be connected directly to the surgical robot 400, for example, via USB cable 309 (or other cable type). Alternatively, the dongle 300 may transmit signals wirelessly to the surgical robot 400, for example, via RF communication whereby a receiver positioned on the surgical robot computer receives the signal from the communication dongle 300. The communication dongle 300 gathers data, for example, from the torque/compression sensing adapter 12, including measurements of the torque applied to the instrument 10. This data is then relayed by the dongle 300 to the computer, which processes and provides the data to the user, for example, on the display 428 for the surgeon's review.

Figure 34:
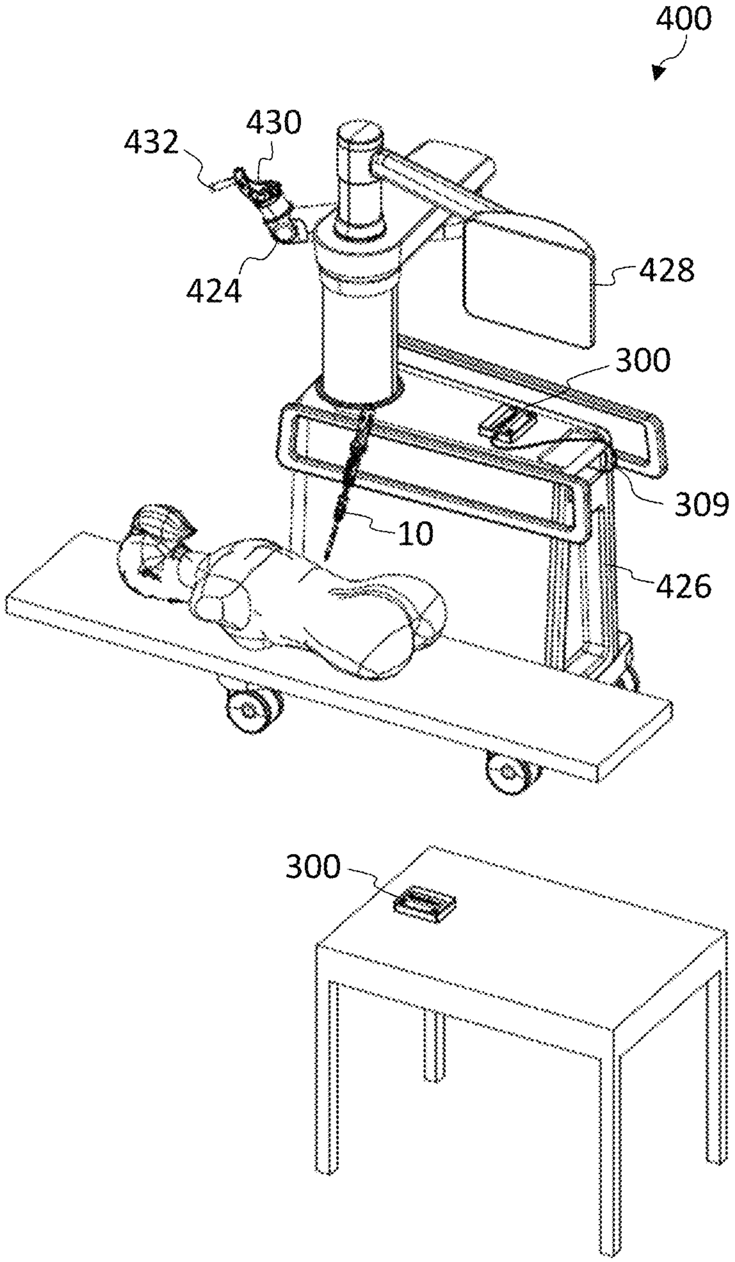
FIG. 34 shows two communication dongles in communication with the smart instrument and surgical robot according to one embodiment.

In another embodiment shown in FIG. 34, two communication dongles 300 may be utilized in the operating room simultaneously. One dongle 300 may be connected to the surgical robot 400 via USB cable 309 and the second dongle 300 may be positioned elsewhere in the operating room. The smart surgical instruments, such as smart screw driver 10, may communicate to each communication dongle 300 separately. The wirelessly positioned communication dongle 300 may receive the signals from the smart instruments 10 and then transmit them to the communication dongle 300 connected to the surgical robot 400. Simultaneously, the communication dongle 300 connected to the surgical robot 400 may be receiving the same communication signals directly from the smart instruments, such as smart screw driver 10. In this configuration, there is redundant transfer of data between the smart instruments and the computer on the surgical robot 400. This redundancy may be beneficial to mitigate loss of data during use. If something causes a data packet to be missed by one communication dongle 300, then the second communication dongle 300 acts as a backup to ensure that the information is not lost.

Force-Sensing Spreader

Figure 35:
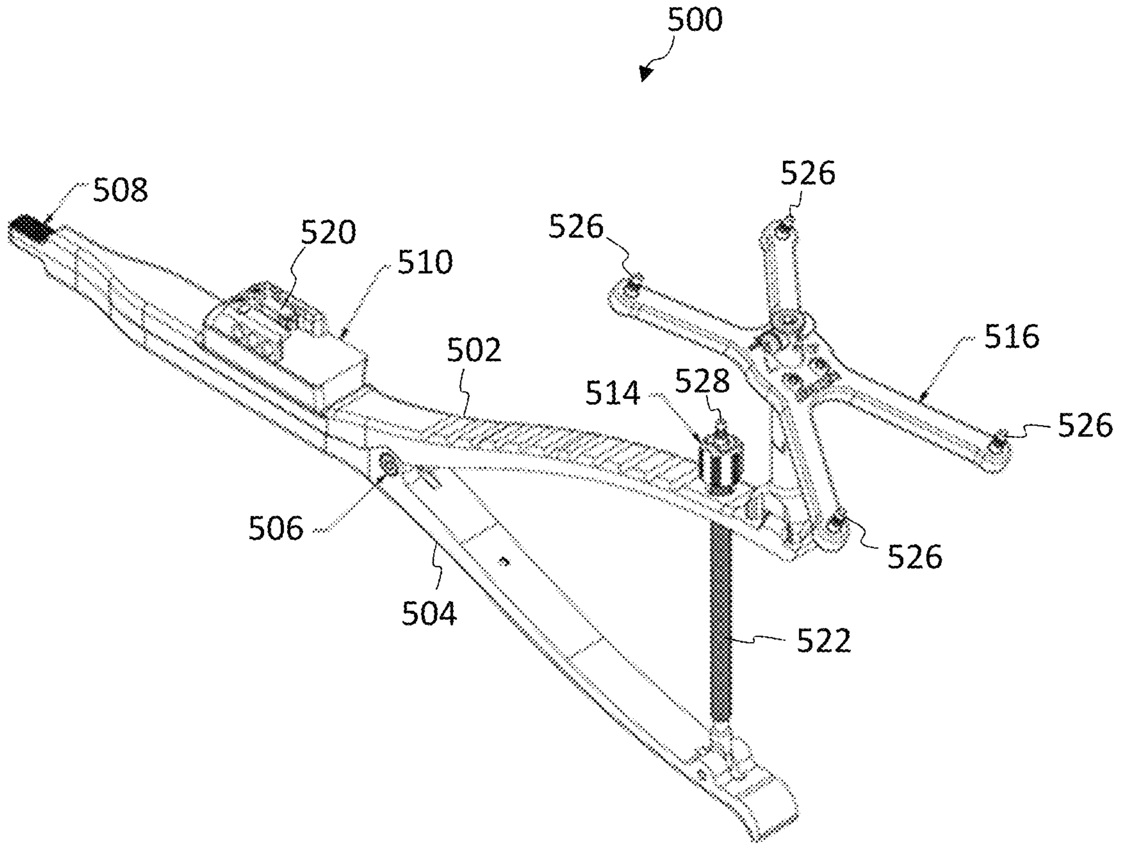
FIG. 35 shows a smart spreader instrument with built-in force measuring according to one embodiment.

Turning now to FIG. 35, a force-sensing spreader instrument 500 is shown according to one embodiment. The spreader instrument 500 may include built-in force measuring, wireless communication, and navigation tracking. The spreader instrument 500 includes two arms 502, 504 connected by a hinge 506, a distal tip 508 designed to engage bony elements of the spine, a spring (not shown), a sealed electronic housing 510 containing PCBA(s) 512, a stop mechanism 514 with a reflective marker, and a navigation array 516 with reflective markers. The distal tip 508 of the instrument has geometry designed to engage different bony elements of the spine including, but not limited to, the spinous process, lamina, or vertebral body. The two arms 502, 504 of the instrument may be connected to a spring (not shown) to keep the distal tips 508 of the instrument 500 closed at rest. The first and second arms 502, 504 may each define a handle portion toward the proximal ends, which are configured to be gripped and squeezed by the user. The stop 514 may include a threaded shaft 522 with a nut 524 to hold force applied to the tip 508. Alternatively, a ratchet with a linear body or rail with a plurality teeth engaged by a pawl may be used to incrementally maintain the position of the distal tip 508 and the amount of force applied to the bones.

Figure 36:
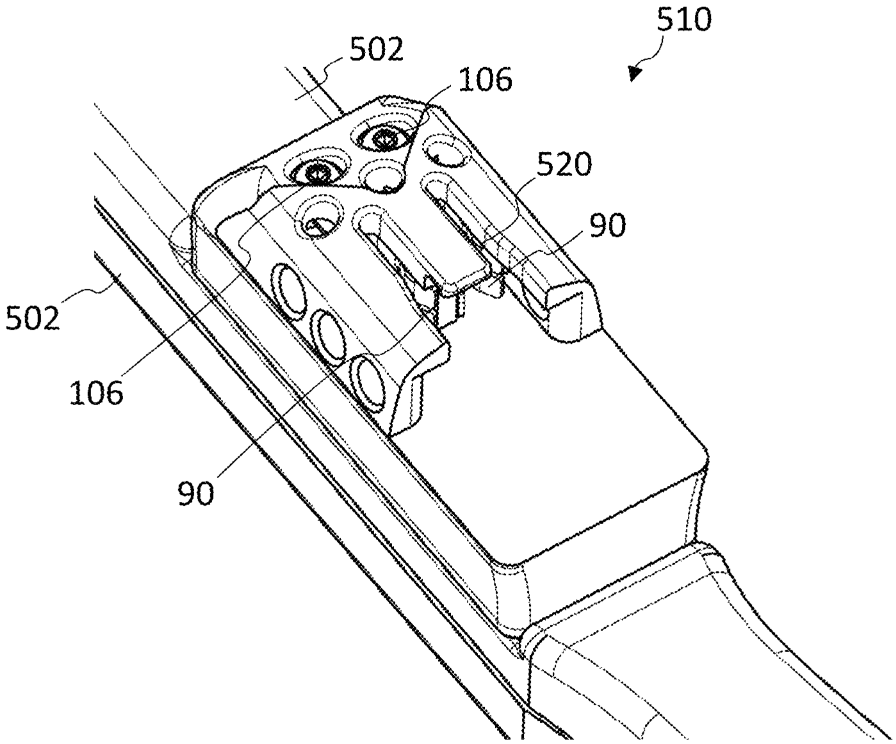
FIG. 36 shows a close-up of the electronic housing for the spreader instrument.
Figure 37:
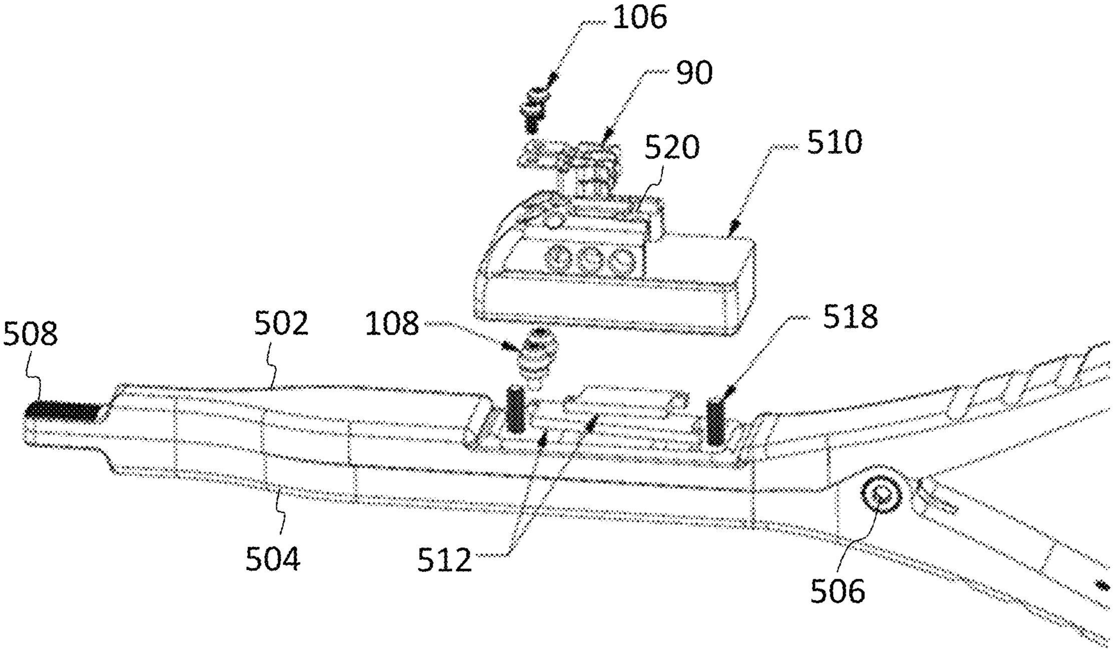
FIG. 37 shows an exploded view of the electronic housing for the spreader instrument.

With further emphasis on FIGS. 36-37, the electronic housing 510 may house the electronic components for the instrument 500. One arm 502 of the instrument 500 may include an area to which strain gauges are mounted, that is sized in cross sectional area such that bending strain values relating to spine stiffness can be discerned. Strain gages are secured to a strain bridge to measure the strain experienced by the instrument 500 when applied to the spine. The strain gages are connected with wires to the PCBA(s) 512 positioned in close proximity to the sensing portion of the instrument 500. This area may be hermetically sealed via epoxy, a gasket, or potting to prevent moisture ingress. The housing 510 may be fixed to the spreader instrument 500 with screws 518 or other suitable means to improve gasket sealing. The electronic housing 510 includes a battery recess 520, similar to battery recess 192, configured to mate with the battery cartridge 18 described above. The battery cartridge 18 may be securely coupled to the instrument 500 when in use. The user aligns and inserts the battery cartridge 18 into the battery recess 520 on the instrument 500, engaging the metal blades 36 on the battery cartridge 18 with the metal contacts 90 on the instrument 500. As previously described, contact between the metal blades 36 in the battery cartridge 18 and the metal contacts 90 on the spreader instrument 500 completes the electric circuit and provides power to the PCBAs 512 positioned within the electronic housing 510.

Figure 38A:
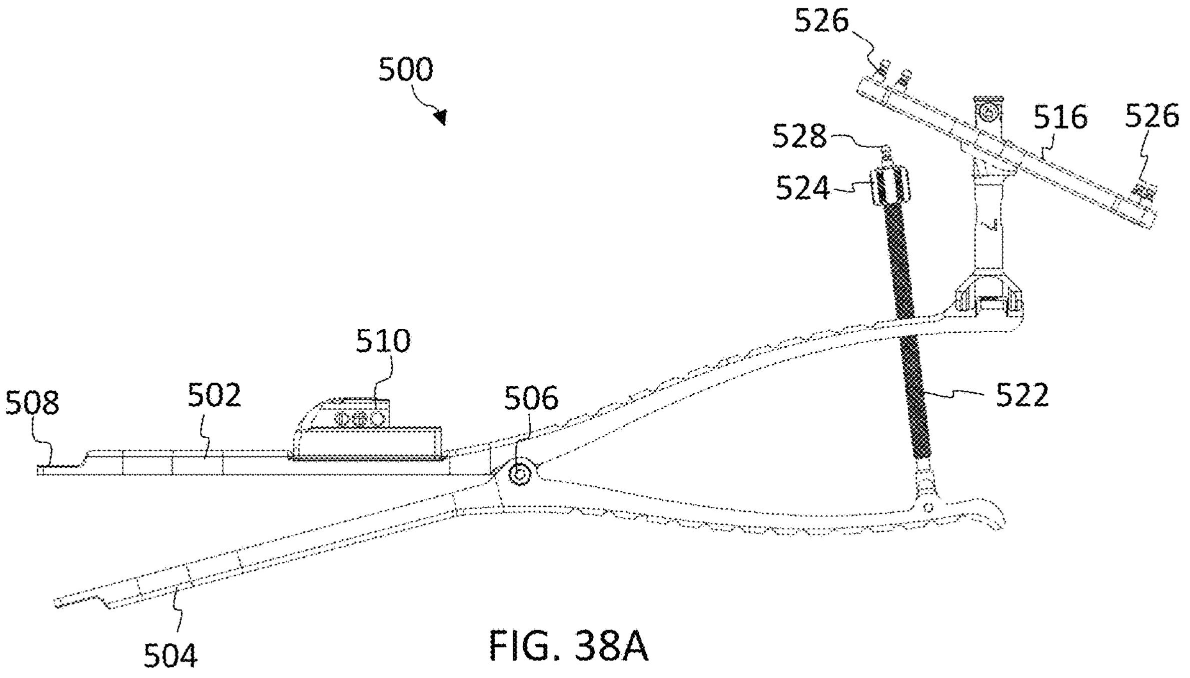
FIGS. 38A-38B show the smart spreader instrument in the open and closed positions, respectively, with tracking spheres.
Figure 38B:
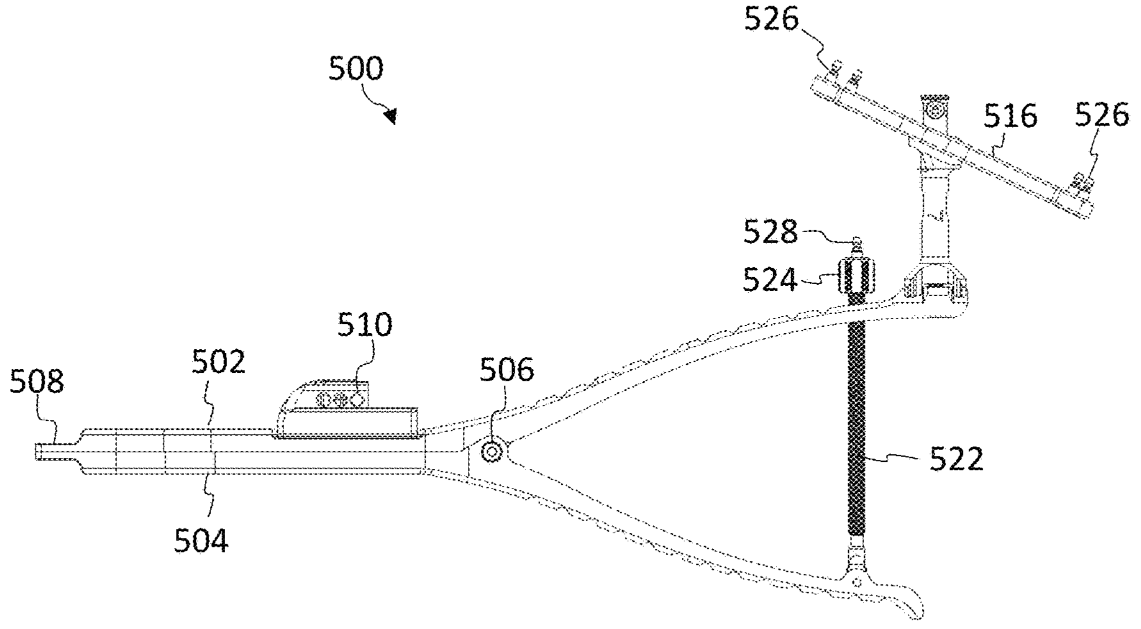

With further reference to FIGS. 38A-38B, the spreader instrument 500 may be tracked via navigation tracking array 516. The navigation array 516 may be permanently affixed to the instrument 500 or it may be reversibly attachable thereto. The array includes posts 526 for supporting reflective markers or active infrared LED's that can be tracked by a camera located in the operating room. Trackable markers may include radiopaque or optical markers, for example. The tracking markers may be suitably shaped, including spherical, spheroid, disc, cylindrical, cube, cuboid, or the like. Alternatively, machine vision may be employed to track the instrument without any markers. In one embodiment, the instrument 500 may be compatible with existing navigation techniques, for example, using robotic navigation system 400 (e.g., Excelsius GPS). The array 516 is used to track the position of the instrument 500 throughout the surgery. The stop 514 may also have a post 528 for supporting a reflective marker or active infrared LED on the stop mechanism 514. This additional marker allows the system to track the distance that the distal tips 508 are open. This may be done by calculating the relationship between the current position of the stop marker and the current position of the array markers since the distance between them changes depending on how far the distal tips 508 are open (e.g., as shown in FIG. 38A). The marker located on the stop mechanism 514 may also be fixed anywhere on the opposing arm to the array 516, similarly able to be positionally tracked with respect to the array 516 during use.

Stiffness may be calculated as the applied force divided by the deflection. Software on the external computer receives the strain data from the instrument 500 to calculate the applied force and position data from the camera to calculate the deflection. Therefore, the system is able to calculate segmental spine stiffness at the level where the instrument 500 is used. The surgeon may move between different levels of the spine and use the instrument 500 to measure segmental spine stiffness at each level. Since the system can track the position of the instruments, the system may automatically calculate and record spine stiffness at each level without any prompts from the user. The spine stiffness measurements may be displayed on screen 428 to the user in various formats such as actual measurements or graphical depictions of relative stiffness for each spine level.

Force-Sensing Rod Reduction Instrument

Figure 39A:
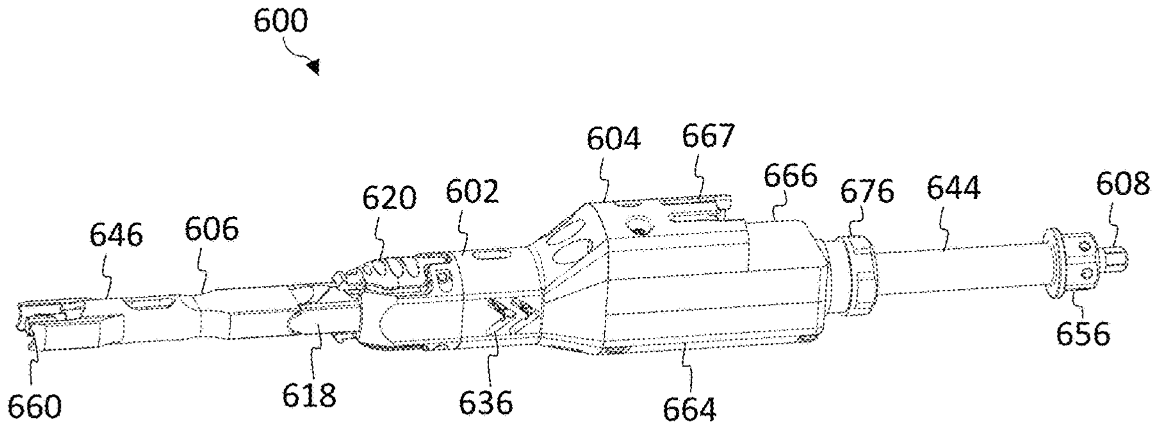
FIGS. 39A-39B show assembled and exploded views, respectively, of a smart compression sensing reducer according to one embodiment.
Figure 39B:
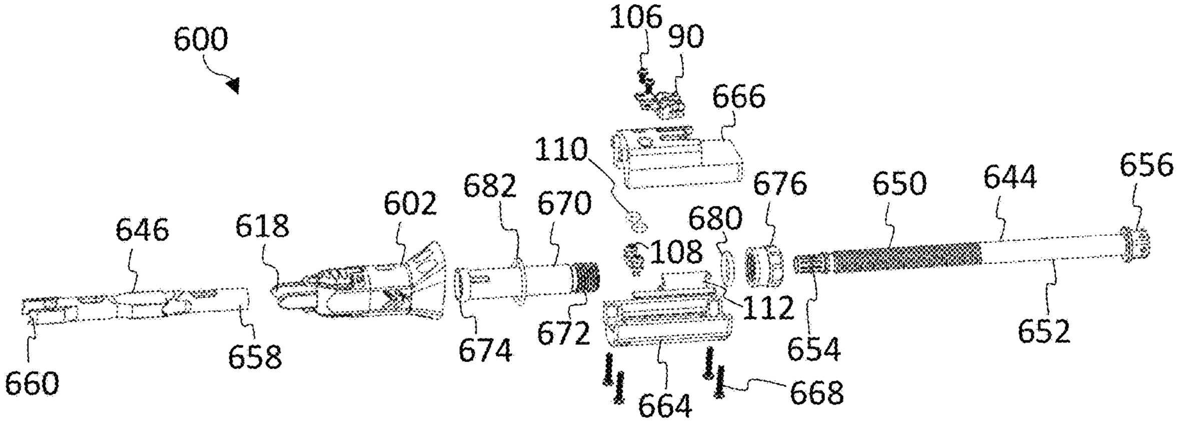
Figure 40:
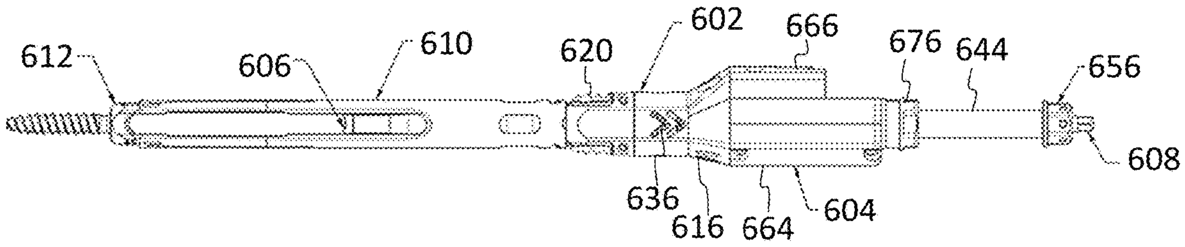
FIG. 40 shows the compression sensing reducer with the mating implant and instrument.

Turning now to FIGS. 39A-39B, a smart compression-sensing rod reduction instrument 600 is shown according to one embodiment. The smart rod reducer instrument 600 is capable of measuring compression loads, when correcting a spinal misalignment. The rod reducer instrument 600 may include a mechanical housing 602, an electronic housing 604, a rod pusher 606, and a locking cap driver 608. As best seen in FIG. 40, the smart rod reducer 600 is configured to couple to an access instrument, such as a minimally invasive surgical (MIS) tower 610. The rod pusher 606 is configured to push a spinal rod (not shown) into an implant 612, such as the head of a pedicle screw head, and once seated therein to be able to insert a locking cap (not shown) into the screw head, capturing the spinal rod. Further details on rod reduction is provided in U.S. Pat. Nos. 11,723,698 and 11,766,281, which are incorporated by reference herein in their entireties for all purposes.

The smart rod reducer instrument 600 provides surgeons with precise measurements of surgical parameters, such as correction force and rod reduction force during spinal surgeries. Data regarding the forces applied during manipulation of spinal rods or correction of spinal alignment is accurately captured in real-time. This capability allows surgeons to make informed decisions during the procedure, adjusting their techniques to optimize surgical outcomes. For instance, by knowing the exact force being applied, a surgeon can avoid overcorrection or under correction, which can reduce the risk of complications and improve the precision of spinal alignments. Moreover, this data can be recorded and analyzed post-operatively to assess the effectiveness of surgical techniques and for educational purposes.

Figure 41:
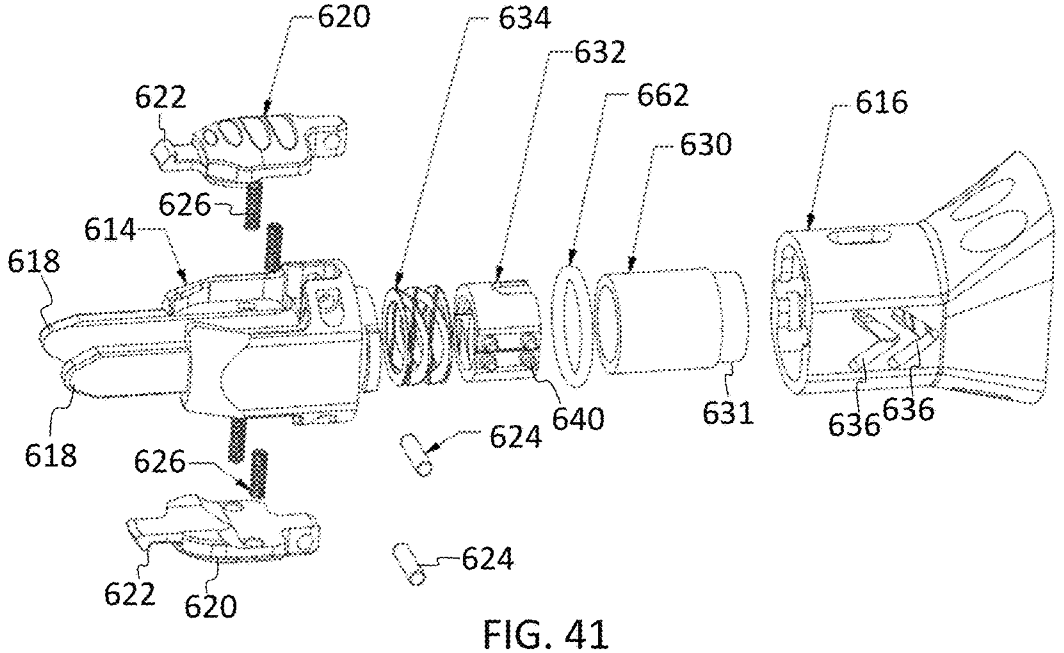
FIG. 41 shows an exploded view of the mechanical housing for the reducer.

The mechanical housing 602 attaches to cut outs on the proximal end of a separate screw access instrument, such as a minimally invasive surgical (MIS) tower 610. As best seen in FIG. 41, the mechanical housing 602 includes a lower half 614 and an upper half 616. The lower half 614 may include a hollow body sized and dimensioned to receive the rod pusher 606 therethrough. The lower half 614 includes a pair of keying prongs 618 extending outward and configured to fit into the MIS tower 610. The keying prongs 618 on the reducer housing 602 may include parallel blades that interface with corresponding through slots on the tower 610 to prevent rotation during usage. The mechanical housing 602 may attach to the tower 610 via releasable spring clips 620. For example, a pair of release clips 620 may be provided on opposite sides of the lower half body 614. Each release clip 620 includes an arm with a hook 622 configured to secure the housing 602 to the tower 610. The release clips 620 are pivotably mounted to the lower half 614 via respective cylindrical pins 624. The clips 620 are spring loaded via springs 626 to bias the clips 620 outward and into engagement with the tower 610.

The upper half 616 of the mechanical housing 602 includes a hollow body sized and dimensioned to receive the rod pusher 606 therethrough and hold other components therein. In particular, the mechanical housing 602 retains a load cell 630, a pair of half nuts 632, and a spring 634. The sidewalls of the upper half 616 define grooves or slots 636 configured to guide movement of the half nuts 632. In particular, an outer surface of the half nuts 632 may include one or more pins 640 configured to ride along the slots 636 to thereby translate the half nuts 632 into or out of engagement with the rod pusher 606. Each half nut 632 may include semi-cylindrical portions or two symmetrical halves of a cylindrical body. When combined they form a complete circular or near-circular profile allowing them to enclose the rod pusher 606. Each half nut 632 may define interior threads 638 configured to engage corresponding threads 650 on the rod pusher 606.

Figure 42:
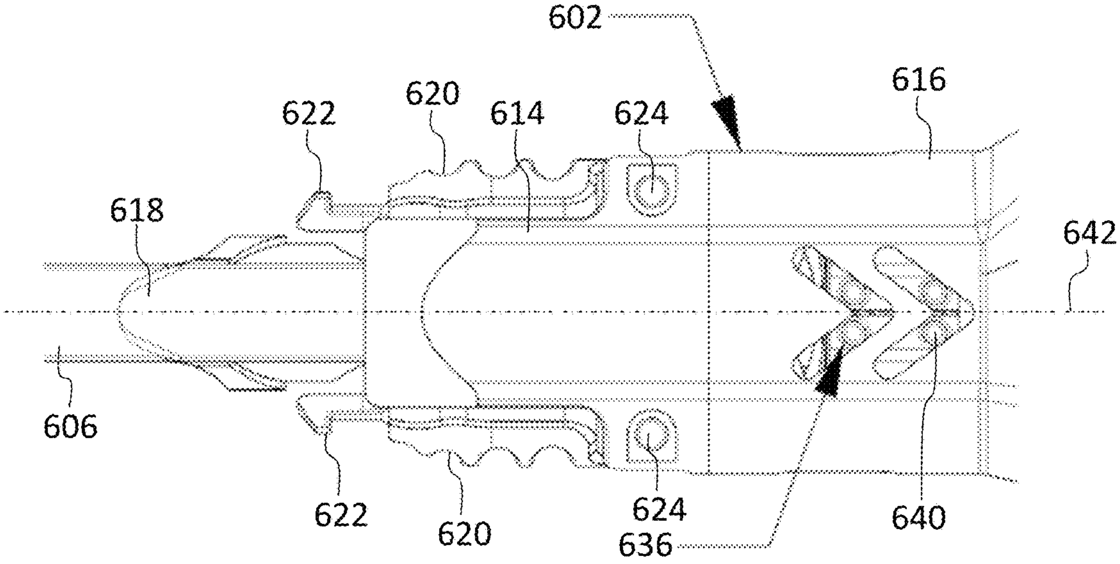
FIG. 42 shows a close-up view of the pin slots in the mechanical housing of the reducer for translating the half nuts within.
Figure 43:
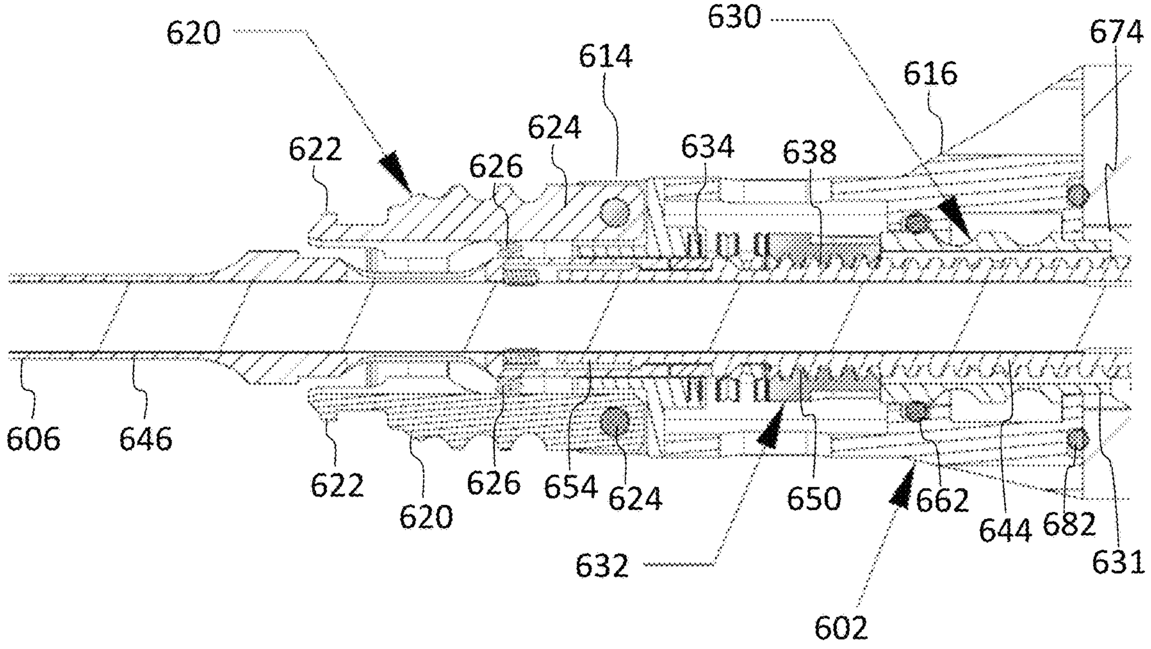
FIG. 43 shows a cross-sectional view of the assembly including the half-nut mechanism.

The pins 640 may include a pair of pins that protrude radially outward from each side of the half nut 632, which are configured to fit in corresponding slots 636. For example, an upper half nut 632 may include a first pin 640 configured to fit in a first slot 636 and a second pin 640 in a second slot 636 on one side with a complimentary pair of pins 640 and slots 636 on the opposite side. Similarly, the lower half nut 632 may mirror the upper half nut 532 with first and second pins 640 that fit in separate portions of the first and second slots 636 in the housing 616. As best seen in FIG. 42, the slots 636 may be slanted or angled to translate the respective half nuts 632 away from the centerline 642 of the instrument 600, for example, when moved distally. For example, each slot 636 may have a V-shape converging at the proximal end and separating apart toward the distal end. In this manner, when moved distally, the two pins 640 of the upper nut 632 travel along the two respective slots 636 upward and the two pins 640 of the lower nut 632 travel along the two respective slots 632 downward. It will be appreciated that similar engagement between the pins 640 and slots 632 occur on the back side of the device. In this manner, as the half nuts 632 travel distally, the pins 640 ride along the slots 632, thereby causing the half nuts 632 to separate apart from one another and disengage from the threaded shaft 644.

The main body of load cell 630 may include a cylindrical tube configured to detect mechanical loads. Similar to load cell 128, load cell 630 may include openings, relief cuts, or the like to maximize load detection, and one or more sensors or gages may be utilized to detect the load. The load cell 630 is configured to fit around the pusher assembly 606, proximal to the half nuts 632, and distal to a central shaft 670. The proximal end of the load cell 630 may include a reduced diameter 631 configured to fit within the end of the central shaft 670. The half nuts 632 may be spring-loaded axially toward the load cell 630 via spring 634.

The rod pusher assembly 606 may include a longitudinal rod pusher shaft 644 and a rod advancer 646, which are aligned with the central axis of the instrument 600. The longitudinal shaft 644 includes a hollow tube with a lumen therethrough configured to receive the locking cap driver 608 therethrough. The longitudinal rod pusher shaft 644 may include an externally threaded section 650, which is configured to interface with the half nuts 632. The longitudinal shaft 644 may also include a non-threaded section 652, which extends proximally from the housing 604. Alternatively, the rod pusher shaft 644 may be fully threaded along its length, for example, as shown for offset reducer 700. The longitudinal rod pusher shaft 644 may further include a distal connector end 654, which mates with the rod advancer 646 at one end, and a proximal reduction driver 656, which can be manipulated to rotate and/or translate the rod pusher shaft 644 at the other end. The rod advancer 646 includes a hollow body with a proximal attachment end 658 and a distal rod-contacting end 660. The attachment end 658 may include a tube that fits through the mechanical housing 602 and is configured to receive the connector end 654 of the rod pusher shaft 644. The distal rod-contacting end 660 may include reduction legs with a recess sized and dimensioned to contact the spinal rod or other suitable interface.

In order to push the spinal rod into the implant 612, threaded components 650 on the pusher 606 interface with threaded components in the housing 602. Threading the rod pusher 606 with respect to the housing 602 propels the spinal rod into the implant 612. The threaded mechanism in the housing 606 may be releasable via the spring-loaded, ramped half nut mechanism 632. When axial force is applied to the pusher 606 in the distal direction, the half nuts 632 are forced into an open state by translating in the ramped slots 636 away from the centerline 642, allowing the threaded pusher 606 to bypass the threads of the housing 602. In the open state, the half nuts 632 are disengaged from the rod pusher assembly 606. When axial force is applied to the pusher 606 in the proximal direction (reduction load), the half nuts 632 are forced into a locked state by translating in the ramped slots 636 towards the centerline 642. In the locked state, the threads 638 of the half nuts 632 are engaged with the threads 650 of the rod pusher assembly 606.

When the instrument is loaded as previously described and the half nuts 632 are in the locked position, they interact with the compression load cell 630 such that force is transmitted from the half nuts 632 to the load cell 630. Strain gages are positioned on the load cell 630 such that the force exerted on the rod during reduction (rod reduction force) can be determined from the strain on the load cell 630. The distal end of the load cell 630 may be hermetically sealed on the outer diameter, in this case with O-ring 662.

Figure 44:
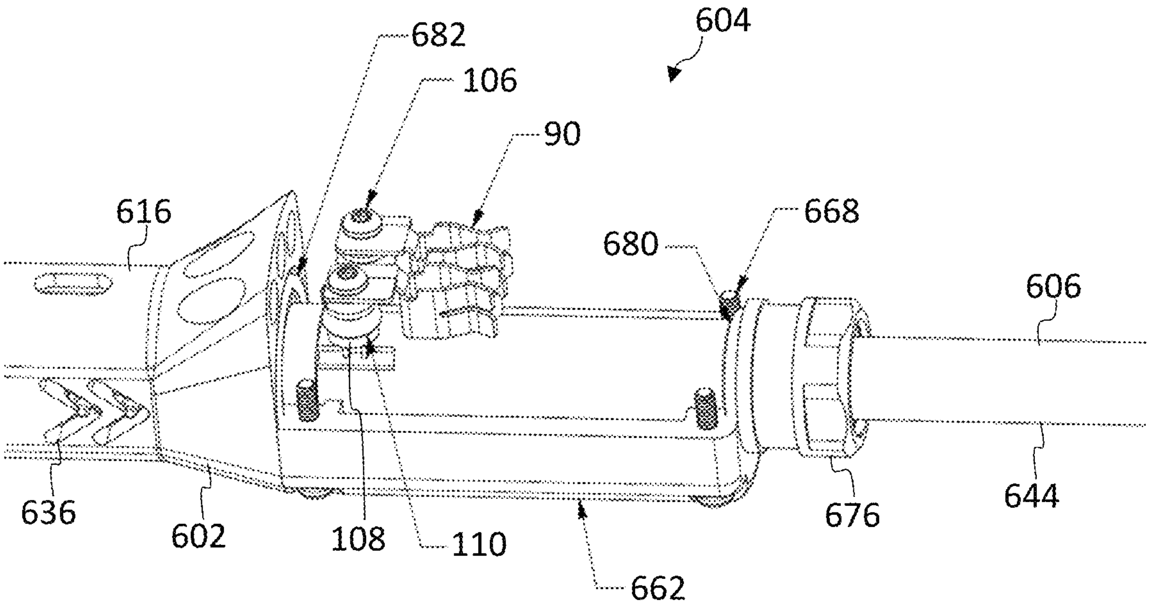
FIG. 44 shows a close-up view of the electronic housing with the top half hidden.

The electronic housing 604 is similar to adapter 12 and housing 510 previously described. The electronic housing 604 includes a lower enclosure half 664 and upper enclosure half 664. FIG. 44 shows a close-up view of the electronic housing 604 with the top half 664 omitted for clarity. The lower enclosure half 664 may have a rectangular body with a U-shaped cross-section to house the components therein. The lower enclosure 664 may be secured to the upper enclosure 666 with screws, bolts, or other fasteners 668. For example, four threaded screws 668 may be used to secure the enclosure pieces 664, 666 together.

Figure 45:
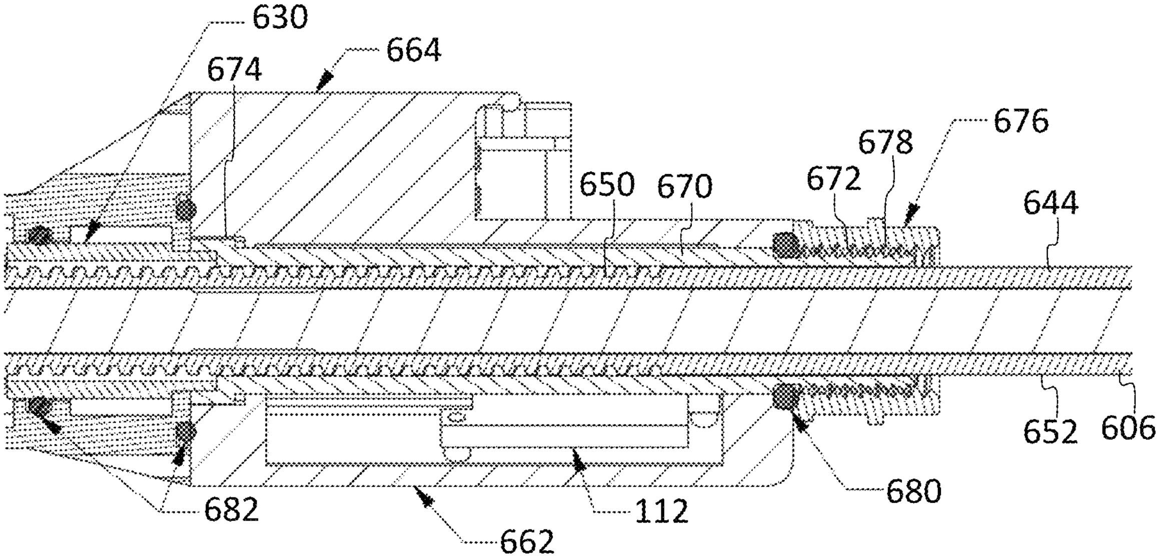
FIG. 45 shows a cross-sectional view of the electronic housing.

The enclosure 664, 666 is configured to receive central shaft 670, which supports the rod pusher 606 therethrough. The central shaft 670 may include a hollow tube defining a lumen dimensioned to receive the rod pusher shaft 644. The central shaft 670 includes an externally threaded end 672 at one end and a collar 674 at the opposite end. The instrument 600 may also contain a tightening nut 676 that is coupled to the central shaft 670. The tightening nut 676 includes a threaded hole 678 that secures the central shaft 670 to the assembly. As best seen in FIG. 45, the tightening nut 676 is threaded onto the threaded end 672 of the central shaft 670 and butts up against the enclosure 664, 666. An O-ring 680 is positioned between the tightening nut 676 and the electronic housing 604 to prevent moisture from entering the interior of the enclosure 664, 666. The load cell 630 is secured to the other end of the central shaft 670. For example, the reduced diameter end 631 of the load cell 630 may be fitted into a recess in the collar 674 of the central shaft 670.

The mechanical housing 602 is coupled to the electrical housing 604. An O-ring 682 may be positioned between the housings 602, 604 to further maintain a tight seal between the components and prevent moisture entry. The components within electrical housing 604 may be similar to those previously described for instrument 10. The metal contacts 90 may be coupled to metal pass throughs 108 via threaded screws 106. O-rings 110 are positioned around the metal pass throughs 108 to prevent moisture from entering the inside of the housing 604. The pass throughs 108 are coupled to the printed circuit board assembly (PCBA) 112. This completes the electric circuit and allows the battery cartridge 18, when installed, to power the PCBA 112 located within the housing 604.

Wires connect the load cell 630 to the PCBA 112 up through the mechanical housing 602 and into the electronic housing 604 where the PCBA 112 resides. The PCBA 112 is powered by the battery cartridge 18 as described above and has an antenna to wirelessly transmit the signals received by the strain gage(s). The signals from the strain gage(s) may be processed and information may then be sent via RF communication (Bluetooth, Wi-Fi, Zigbee, etc.) to an external communication receiver. The electronic housing 604 may be composed of plastic or other RF compatible material to allow the antennae on the PCBA 112 to send signals out from the instrument 600.

The lower enclosure half 664 of the electronic housing 604 may secure the PCBA(s) 112 inside the enclosure. The lower enclosure half 664 may have bosses that fit into through holes in the PCBA. The upper enclosure half 666 of the electronic housing 604 mates with the battery cartridge 18 in a manner similar to instruments 10, 500. For example, a battery recess 667 defined along an outer surface of the upper enclosure 666 may define a plug shaped recess sized and dimensioned to receive the battery cartridge 18. The metal contacts 90 and metal pass throughs 108 are secured within the upper enclosure half 666. O-rings 110 are positioned around the metal pass throughs to seal the enclosure cavity.

The upper enclosure half 666 is configured to mate with the battery cartridge 18 such that the battery cartridge 18 is securely coupled to the instrument 600 when in use. The user aligns and inserts the battery cartridge 18 into the recess 667 on the instrument 600, engaging the metal blades 36 on the battery cartridge 18 with the metal contacts 90 in the instrument 600. Contact between the metal blades 36 in the battery cartridge 18 and the metal contacts 90 in instrument 600 completes the electric circuit and provides power to the PCBA 112.

The upper and lower enclosure halves 664, 666 may have geometry along their borders to create a seam, similar to seam 196. The seam may be sealed during assembly to prevent moisture from entering the interior of the enclosure. The seam may be sealed by epoxy, ultrasonic welding, or other techniques. Alternatively, the interior cavity of the enclosure 664, 666 could be potted with silicone or a similar material to protect the electronics from moisture.

Figure 46:
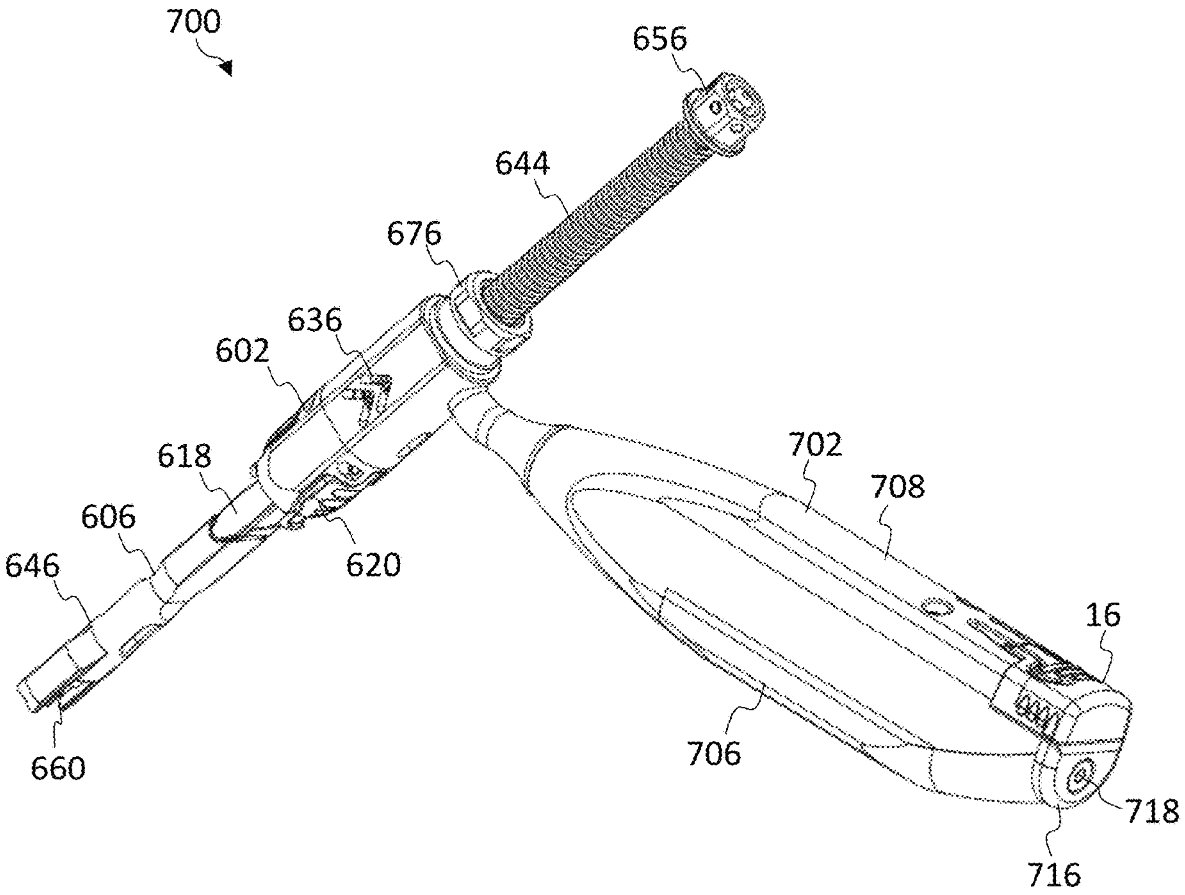
FIG. 46 shows the force sensing reducer with an integrated offset deformity correction handle according to one embodiment.
Figure 47:
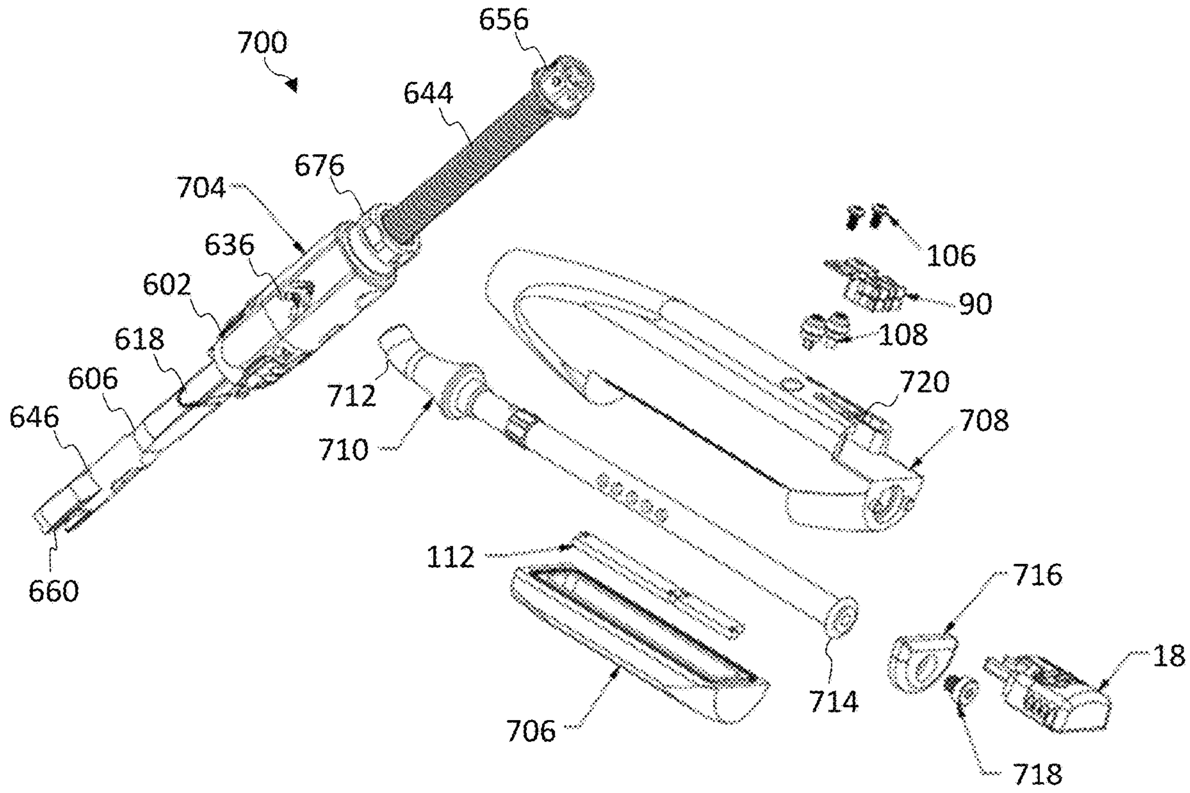
FIG. 47 shows an exploded view of the deformity correction handle assembly.

Turning now to FIGS. 46-47, an alternative smart rod reduction instrument 700 is shown according to one embodiment. In the above embodiments, the electronic housing is in line with the central axis of the instrument. In this embodiment, the instrument 700 includes the same reduction instrument and electronic components; however, the electronic housing is in the form of a handle 702 offset laterally from the remainder of the instrument. The reducer portion 704 includes the same functional components as reducer instrument 600 including main housing 602 with load cell 630 and half nuts 632, and the rod pusher assembly 606 aligned along the instrument axis to reduce the spinal rod into the implant 612. The handle 702 is offset to the reducer 704 and may be used for deformity correction maneuvers or other screw manipulation maneuvers used in spinal procedures.

As best seen in FIG. 47, the handle 702 may include a bottom half 706 and a top half 708, thereby forming the ergonomic handle and the electrical enclosure for the battery lead components (e.g., contacts 90, pass throughs 108, and PCBA 112). A handle core 710 may have a connection end 712, which connects to the housing 602 of the reducer 704, and a terminal end 714, which acts as the free end of the handle 702. The handle core 710 may be a tube or other suitable structure for supporting the enclosure halves 706, 708 and a conduit for wiring of the electrical components. A handle cap 716 may connect to the base of the top half 708 and the terminal end 714 of the core 710 with a screw 718, for example. The handle top half 708 includes a battery recess 720, similar to battery recess 192, 667, configured to receive the battery cartridge 18, which completes the electrical circuit and allows the battery cartridge 18 to power the PCBA 112.

The reduction instrument may also incorporate a secondary load cell to measure bending force. This may be used to accomplish a bending force correction goal in conjunction with a biokinematic model or may be used to monitor the construct to avoid adverse effects from the correction maneuver. An advantage of this embodiment is that the overall height of the instrument is reduced, as now all of the electronics are stored offset from the functional components of the instrument.

The current state of the art techniques for spine deformity correction surgery rely heavily on surgeon judgment to make safe and effective decisions intraoperatively. Surgeons use their best judgement when assessing bone-screw interface strength, spine stiffness, correction goals, bone removal requirements, and other key factors relating to spine surgery. Due to the subjective nature of these decisions, different surgeons may achieve different results based on their level of experience and history with similar clinical presentations, which may or may not result in optimal clinical outcomes for the patient. Therefore, it would be advantageous for surgeons to have tools that take some of the subjective guesswork out of the equation and replace it with analytical measurements of key factors. The devices and methods described herein of measuring intraoperative data related to bone-screw interface strength, correction force, and spine stiffness, for example, aid the surgeon in decision making as well as increase operative safety and efficacy. The smart surgical instruments give surgeons accurate and precise assessments of critical surgical parameters, such as screw insertion torque, segmental and global spine stiffness, correction force, rod reduction force. These metrics provide the surgeon with useful real-time data in order to make safe and effective decisions during surgery. A system of smart surgical instruments allows all surgeons to optimize surgical treatments for their patients regardless of experience level and history.

Orientation Sensing Modules (OSMs)

Figure 48A:
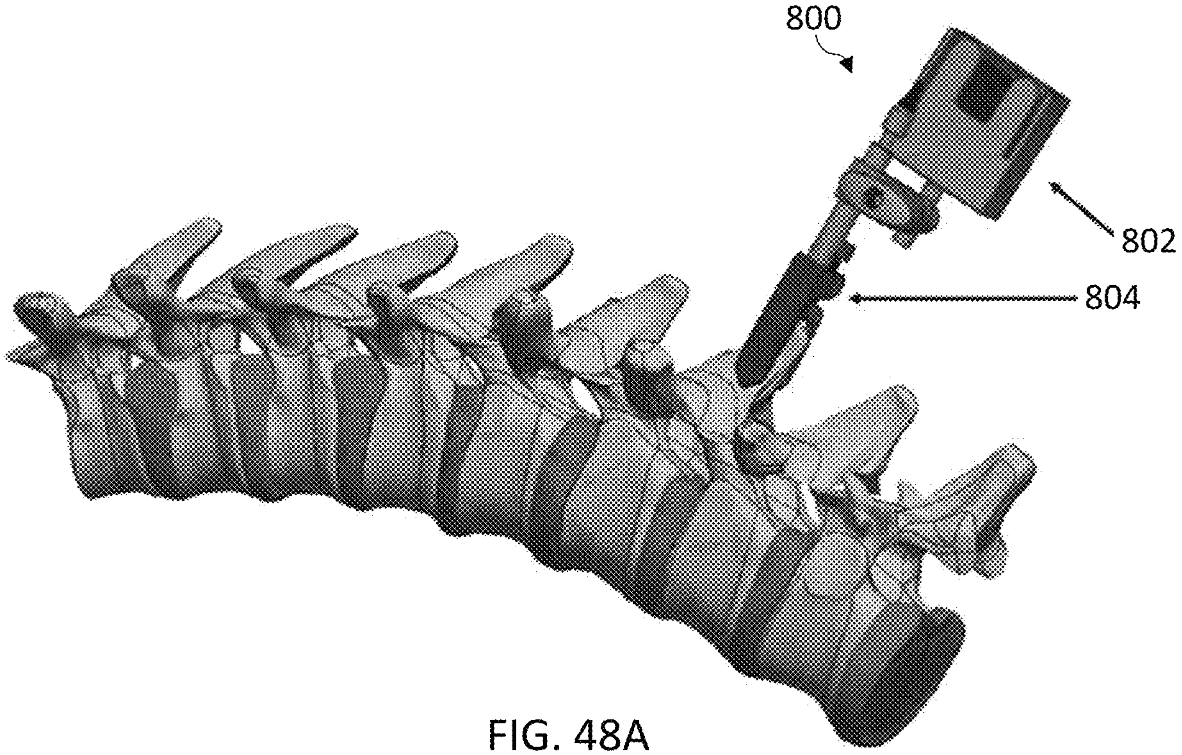
FIGS. 48A-48B show examples of an orientation sensing module attached to a bone clamp affixed to the spine, and attached to a plate with lamina screws, respectively.
Figure 48B:
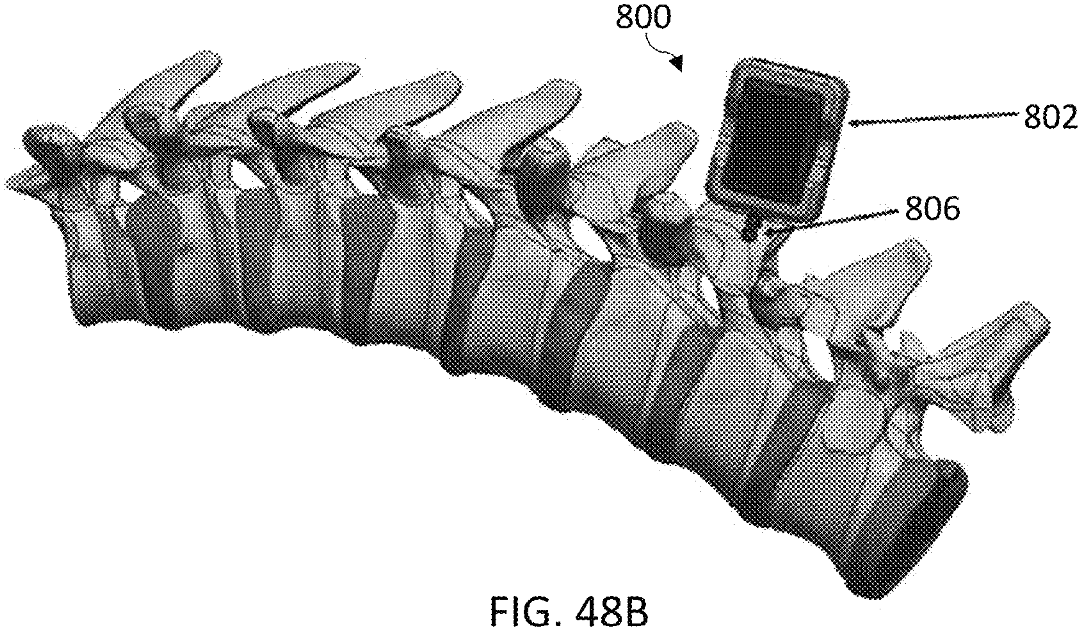

Turning now to FIGS. 48A-48B, a system 800 for actively measuring patient specific spinal alignment intraoperatively is shown. Achieving proper alignment is crucial for the success of spine surgery, patient outcomes, and long-term spinal health. However, the complexity of the spinal anatomy makes measuring alignment a demanding task. The spine consists of multiple vertebrae, discs, joints, and ligaments, each with its own unique characteristics. Assessing the relative position and orientation of these structures in three dimensions can be intricate and requires a thorough understanding of spinal anatomy. Spinal deformities or misalignments often involve rotations and curvatures in multiple planes. Measuring alignment necessitates evaluating the sagittal, coronal, and axial planes to capture the complete three-dimensional picture. During surgery, factors such as patient positioning, muscle relaxation, and surgical manipulation can introduce variability in spinal alignment. Limited visibility in the surgical field, the small working area, and potential obstructions, such as surrounding tissues, blood, or instruments, can make it difficult to visualize and assess alignment accurately. Surgeons often rely on fluoroscopy or other intraoperative imaging techniques to enhance visibility and aid in alignment measurement.

In order to accurately assess and measure the alignment of the spine intraoperatively, system 800 actively measures the alignment of the spine without requiring a direct line of sight, the use of radiation, and minimal surgeon intervention. The system 800 provides the surgeon with real time measurements of the spinal alignment of the patient to help inform further surgical decisions such as additional correction techniques, while limiting exposure to radiation.

Spinal alignment may be measured and communicated wirelessly using Orientation Sensing Modules (OSM) 802. The OSM may contain a nine degrees of freedom (DOF) inertial measurement unit (IMU), a microcontroller, a Bluetooth module, and a battery. The OSMs may be rigidly attached to multiple types of patient fixation devices and connected to a robot and/or navigation system, such as robot 400 (e.g., EGPS or EHUB via Bluetooth). The 9-DOF IMU may include three types of sensors: an accelerometer, a gyroscope, and a magnetometer. By combining the measurements from these sensors, the OSM captures information related to movement, rotation, and orientation. The IMU provides motion tracking by measuring acceleration, angular velocity, and magnetic field data in three-dimensional space.

The accelerometer measurers linear acceleration in three axes (x, y, z) relative to the device's frame of reference, which provides information on the acceleration due to gravity and acceleration due to forces on the device. This helps in detecting motion, tilt, and orientation. The gyroscope measures angular velocity (rotational movement) in three axes (x, y, z) relative to the device's frame of reference, which provides information on the rate at which the device is rotating and changing orientation. This helps track rotation and changes in orientation. The magnetometer measures the magnetic field strength in three axes (x, y, z), which provides information on the orientation of the device with respect to Earth's magnetic field. This is useful for determining absolute orientation with respect to Earth's magnetic field (compass functionality).

The microcontroller may process the raw data from all three types of sensors and run algorithms (e.g., Kalman filter, complementary filter, etc.) to fuse the data to estimate the device's orientation. The fusion of data from all three sensors helps to mitigate errors, reduce drift, and enhance the accuracy and stability of the OSM. The battery can power the device, and the Bluetooth module can wirelessly communicate orientation data to a robot and/or navigation system, such as robot 400 (e.g., EGPS or EHUB). The navigation system may then use the orientation data of multiple OSMs and their starting locations with respect to the anatomy to continuously calculate and display the spinal alignment of the patient.

The OSM 802 may be a single use, disposable device that is inserted into a patient fixation device. The patient fixation devices can be any device that rigidly attaches to the patient's spine. For example, as shown in FIG. 48A, a bone clamp 804 can rigidly attach to the patient's spinous process and may be used with the OSM 802. Alternatively, as shown in FIG. 48B, a device that rigidly attaches to the patient's lamina, such as a plate with lamina screws 806, may be used with the OSM 802. Multiple OSMs and patient fixation devices may be used based on the alignment parameters the surgeon is interested in recording.

Figure 49:
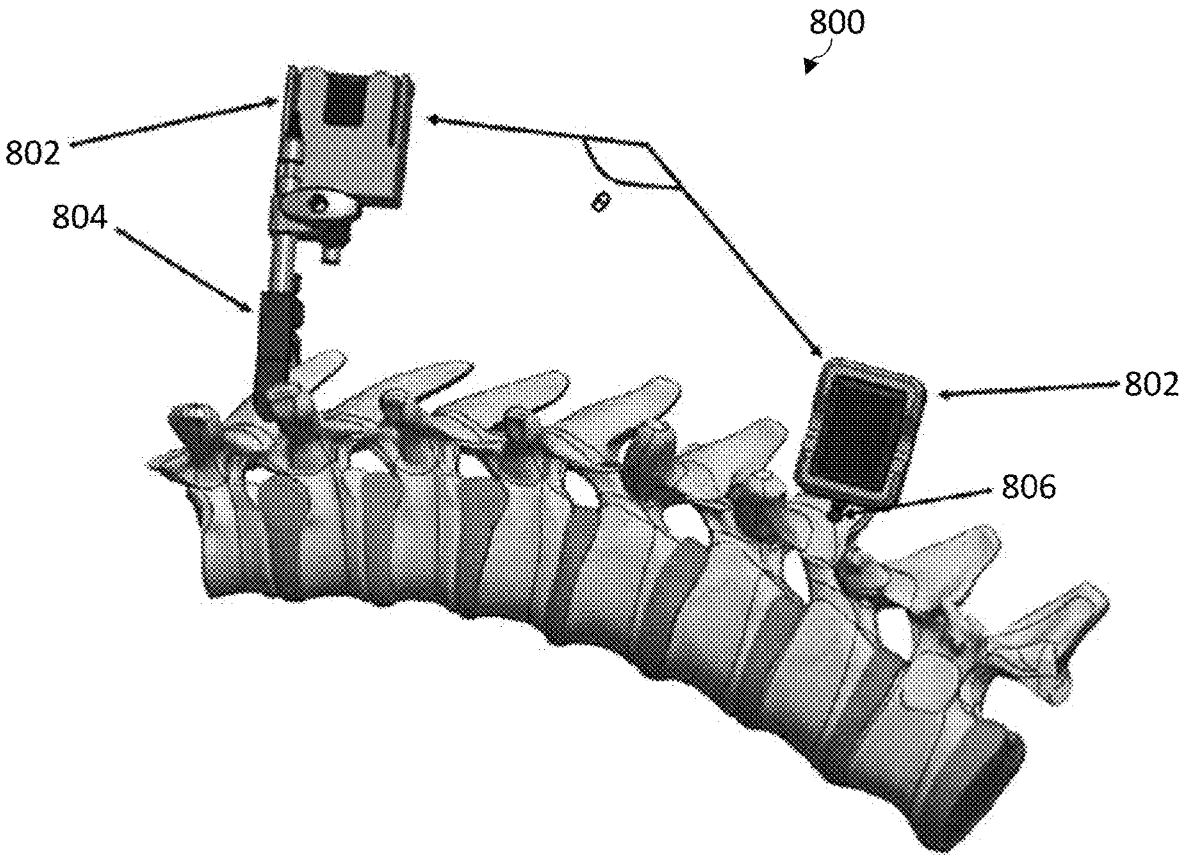
FIG. 49 shows an example of multiple orientation sensing modules attached to the spine to calculate the desired alignment parameters.

In one embodiment, the surgeon may begin by turning on the one or more OSMs 802 and connecting them via Bluetooth to a navigation system, such as robot 400. Once connected, the surgeon can place patient fixation devices 804, 806 with OSMs 802 attached to levels of interest. FIG. 49 shows one example of multiple OSMs attached to different vertebrae, which help to calculate the desired alignment parameters. The surgeon then performs correction techniques to correct deformities or misalignments, creating a change in the position and shape of the spine. The OSMs 802, being rigidly attached to levels of interest, also change position and orientation during the correction (e.g., change 8 including angle and distance between the OSMs). Any change in position and orientation can be measured and communicated to the surgeon by the system 400. While the surgeon is performing correction techniques, they can watch the alignment parameters and shape of the construct change live on monitor 428 or similar viewing device. This can inform the surgeon of how their correction techniques are affecting spinal alignment in real time.

Robotic Intra-Operative Calibration of OSMs

When using sensors like accelerometers, gyroscopes, and magnetometers in the OSM 802, it is beneficial to calibrate the sensors before data collection to ensure data accuracy. Without calibration, various errors, such as zero rate bias, drift, hard iron distortions causing offset errors, soft iron distortions causing scale factor errors, and other inaccuracies, may affect the collected data.

Figure 50:
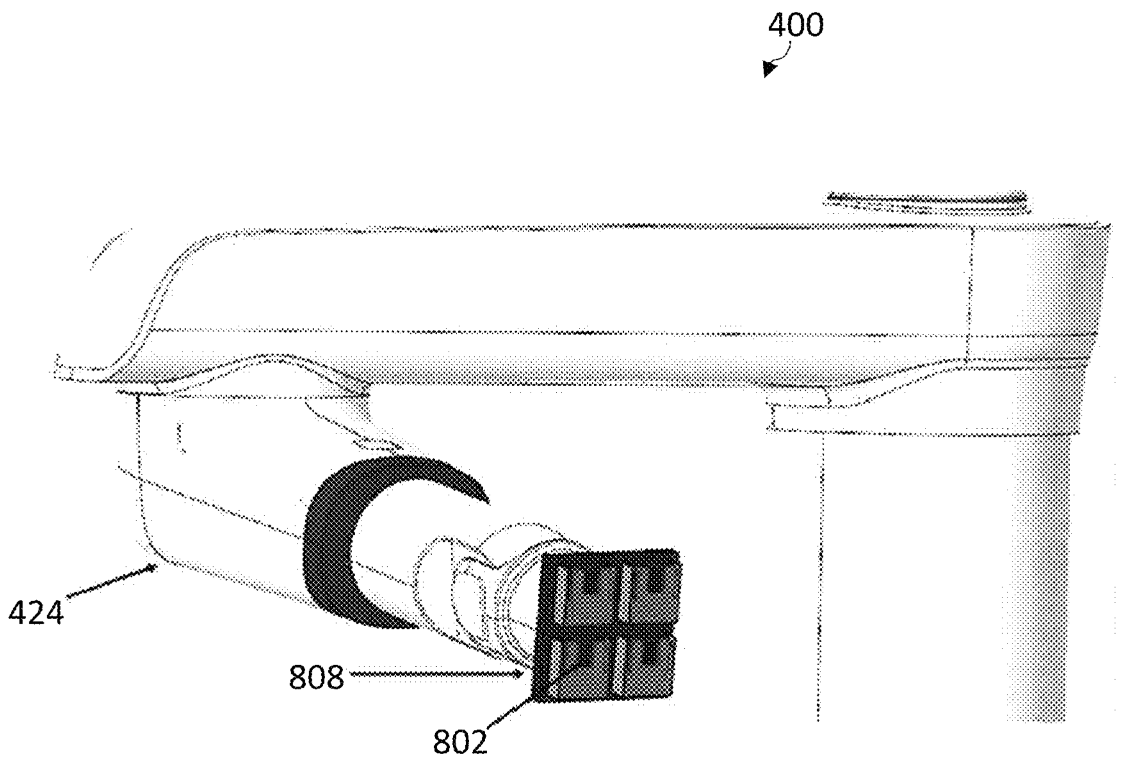
FIG. 50 shows a robot arm with a calibration jig end effector with orientation sensing modules attached according to one embodiment.

In one embodiment, a robot system, such as robot 400 (e.g., Excelsius GPS), may be utilized to perform the calibration of the OSMs 802 intraoperatively to ensure that they are reliably and repeatably calibrated. As best seen in FIG. 50, a calibration jig end effector 808 may be connected to the robot's arm 424 and the user calibrated. The user may attach one or multiple OSMs 802 to the calibration jig 808. Once the OSMs 802 are turned on, connected to the robot 400 via Bluetooth or other means, and attached to the calibration jig 808, the user may then initiate calibration on the robot 400. The calibration may move the robot arm 424 in a series of motions to calibrate the sensors in the OSMs 802. For example, the accelerometer may be calibrated by moving the calibration jig 808 to a stable, level position and holding that position for a few seconds while collecting accelerometer data. This calculates the sensor's bias and scale factors and applies correction to the raw accelerometer data to remove any bias or non-linearity. The gyroscope may be calibrated by holding the calibration jig 808 stationary while collecting gyroscope data, thereby eliminating drift in the gyroscope. The magnetometer may be calibrated by moving the calibration jig 808 away from magnetic materials to reduce magnetic interference and then collecting magnetometer data while rotating the calibration jig 808 in various directions, such as a figure-eight or 360 degrees of rotation. The collected data may be used to compute the hard and soft iron corrections to compensate for magnetic distortions.

Once the robot 400 completes the calibration of each sensor within the OSM 802, it can then validate the calibration by rotating and moving the calibration jig 808 in various orientations and directions. The collected data from the validation step may be directly compared to the expected movement of the robot arm 424 to observe if the data collected is consistent and drift-free. If the validation step passes, the bias offsets, scale factors, and magnetometer calibration data may be stored in both the individual OSMs 802 on the calibration jig 808 and the robot 400 so that the calibration can be applied if the user needs to reconnect the OSMs 802 to the system. These steps ensure that there is no user error in the calibration steps and the collected data is accurate.

These alignment systems allow the surgeons to measure spinal alignment intraoperatively in real time while reducing radiation exposure and operative time due to reduced use of fluoroscopy. By actively measuring spinal alignment intraoperatively, the safety, efficacy, reliability, and repeatability of correction maneuvers during deformity surgery can be improved. The additional information gives surgeons patient specific data they can use to optimize clinical outcome. This information can be aggregated into a database and utilized to improve algorithms for predicting, tracking, and achieving optimal deformity correction.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A smart instrument system for correcting a spinal deformity comprising:

a smart instrument, the smart instrument including:

an elongate handle at a proximal end of the smart instrument;

a driver assembly at a distal end of the smart instrument and configured to apply torque to an implant during a surgical procedure, the driver assembly including a driver shaft with a distal drive tip and a proximal connection end, and an elongate handle arranged between the distal drive tip and the proximal connection end;

a force-sensing adapter assembly arranged between the handle and the driver assembly and configured to sense and measure intraoperative real-time data while the instrument is in use during the surgical procedure, the force-sensing adapter assembly including a proximal end with an attachment interface and a distal female connection end, the proximal end comprising a shaft defining the attachment interface including a geometry shaped to correspondingly mate by quick connection to the handle, the distal female connection end including a collar defining a central bore dimensioned to fit a sleeve and a collet and a driver shaft housing configured to receive the proximal connection end of the driver shaft, wherein the driver shaft housing and the proximal connection end of the driver shaft include corresponding mating geometries which allows the force-sensing adapter assembly to exert a torque or compression on the driver shaft when the instrument is in use, wherein the collet includes ball bearings and exterior threads which thread into corresponding threads within the bore of the collar, wherein the collet is configured to translate axially relative to the sleeve, wherein when in a locked position, the sleeve is translated proximally such that the ball bearings partially protrude into an inner diameter of the collet, and when in an unlocked position, the sleeve is translated distally such that the ball bearings retract into the collet, an enclosure housing a load cell having one or more sensors to accurately measure force and electronically connected to a printed circuit board assembly configured to wirelessly transmit signals; and a battery cartridge receivable in the enclosure of the force-sensing adapter assembly and configured to power the printed circuit board assembly, wherein the handle, the driver shaft and the load cell are coaxial and aligned along a common longitudinal axis defined through the smart instrument;

at least one communication dongle configured to receive signals transmitted by the force-sensing adapter assembly;

and a robot system configured to receive the signals transmitted from the printed circuit board assembly, wherein the real-time data is communicated to a user to provide guidance during the surgical procedure, and wherein the real-time data includes screw insertion torque, segmental and/or global spine stiffness, correction force, and/or rod reduction force.

2. The system of claim 1, wherein the battery cartridge includes a battery enclosure with a pair of metal blades protruding outward, a contact pad coupled to each respective metal blade with a screw, and a battery positioned between the contact pads.

3. The system of claim 2, wherein the battery cartridge includes a protruding arm with a hook configured to mate with a corresponding notch in the force-sensing adapter assembly to securely couple the battery cartridge to the force-sensing adapter assembly.

4. The system of claim 2, wherein the smart instrument includes battery lead components for electrically connecting the battery cartridge to the printed circuit board assembly, the battery lead components including metal contacts each having a U-shaped body which form a receptacle to accept the respective metal blades of the battery cartridge, and metal pass throughs that connect the metal contacts to the printed circuit board assembly.

5. The system of claim 1, wherein the at least one communication dongle includes an enclosure, a printed circuit board assembly, and a battery.

6. The system of claim 1, wherein the at least one communication dongle comprises a first communication dongle connected directly to the robot system and a second communication dongle used simultaneously for redundant transfer of data.

7. A smart instrument for correcting a spinal deformity comprising:

an elongate handle at a proximal end of the smart instrument;

a driver assembly at a distal end of the smart instrument and configured to apply torque to an implant during a surgical procedure, the driver assembly including a driver shaft with a distal tip configured to engage with the implant, a proximal connection end, and an elongate handle arranged between the distal tip and the proximal connection end, a force-sensing adapter assembly arranged between the handle and the driver assembly and configured to sense and measure torque and compression loads in real-time during the surgical procedure, the force-sensing adapter assembly including a proximal end with an attachment interface and a distal female connection end, the proximal end comprising a shaft defining the attachment interface including a geometry shaped to correspondingly mate by quick connection to the handle, the distal female connection end including a collar defining a central bore dimensioned to fit a sleeve and a collet and a driver shaft housing configured to receive the proximal connection end of the driver shaft, wherein the driver shaft housing and the proximal connection end of the driver shaft include corresponding mating geometries which allows the force-sensing adapter assembly to exert a torque or compression on the driver shaft when the instrument is in use, wherein the collet includes ball bearings and exterior threads which thread into corresponding threads within the bore of the collar, wherein the collet is configured to translate axially relative to the sleeve, wherein when in a locked position, the sleeve is translated proximally such that the ball bearings partially protrude into an inner diameter of the collet, and when in an unlocked position, the sleeve is translated distally such that the ball bearings retract into the collet, and an enclosure housing a load cell having one or more sensors configured to accurately measure force without permanent deformation, and a printed circuit board assembly electronically connected to the load cell and configured to wirelessly transmit signals, wherein the load cell includes a torque sensing portion and a compression sensing portion; and a battery cartridge receivable in the enclosure of the force-sensing adapter assembly to power the force-sensing adapter assembly, the battery cartridge comprising two enclosure halves housing a coin-cell battery, two metal blades, two contact pads, and two assembly screws, wherein the two metal blades independently encase with mating metal contacts on the force-sensing adapter assembly allowing the battery to power the printed circuit board assembly.

8. The instrument of claim 7, wherein the torque sensing portion has an area of decreased diameter with strain gages mounted to an outer surface of the load cell.

9. The instrument of claim 7, wherein the compression sensing portion has a through hole cut transversely to a longitudinal axis of the load cell and relief cuts positioned symmetrically around the through hole with strain gages mounted on the outer surface of the load cell between and within the relief cuts.

10. The instrument of claim 7, wherein the load cell includes a thin walled tube positioned within an inner cannulation of the load cell.

11. A smart instrument system for actively measuring patient specific spinal alignment intraoperatively comprising:

at least one single use, disposable smart instrument configured to sense and measure intraoperative real-time spinal alignment data wirelessly during a surgical procedure, each smart instrument comprising a housing containing an inertial measurement unit, a microcontroller, a wireless communication module, and a battery, the inertial measurement unit including an accelerometer, a gyroscope, and a magnetometer that captures data related to movement, rotation, and orientation and provides nine degrees of freedom by measuring acceleration, angular velocity, and magnetic field data in a three-dimensional space; each smart instrument being directly attached to a patient fixation device for rigidly securing the respective smart instrument to a spine of a patient, wherein the patient fixation device is a bone clamp or a lamina plate with screws configured to be rigidly attached to the patient's spine; and a robot system configured to wirelessly receive data transmitted from the at least one smart instrument, wherein the real-time data is communicated to a user on a viewing device to provide guidance to the user during the surgical procedure so that any change in position and/or orientation of the spine during alignment thereof can be measured and communicated to the user by the robot system thereby providing data on the alignment of the spine intraoperatively, and wherein the system is configured to use the data of the at least one smart instrument and its starting location with respect to the patient's anatomy to continuously calculate and display the spinal alignment of the patient during the surgical procedure.

12. The system of claim 11, further comprising a calibration jig attachable to a robot arm of the robot system, and the smart instrument is attachable to the calibration jig to calibrate the accelerometer, gyroscope, and magnetometer based on movements by the robot arm.

* * * * *